(12) United States Patent
Schultz et al.

(10) Patent No.: US 7,462,602 B2
(45) Date of Patent: Dec. 9, 2008

(54) ANTI-SCARRING RIBOZYMES AND METHODS

(75) Inventors: Gregory S. Schultz, Gainesville, FL (US); Alfred S. Lewin, Gainesville, FL (US); Timothy D. Blalock, Boston, MA (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 386 days.

(21) Appl. No.: 10/836,670

(22) Filed: Apr. 30, 2004

(65) Prior Publication Data

US 2004/0235031 A1 Nov. 25, 2004

Related U.S. Application Data

(60) Provisional application No. 60/467,119, filed on May 1, 2003.

(51) Int. Cl.
*A01N 43/04* (2006.01)
*C12Q 1/68* (2006.01)
*C12Q 19/34* (2006.01)
*C07H 21/02* (2006.01)
*C07H 21/04* (2006.01)

(52) U.S. Cl. ............... 514/44; 435/6; 435/91.1; 435/91.31; 435/320.1; 435/455; 536/23.1; 536/24.5

(58) Field of Classification Search .......... 435/6, 435/91.1, 91.31, 455, 458, 320.1; 514/44; 536/23.1, 24.5
See application file for complete search history.

(56) References Cited

U.S. PATENT DOCUMENTS

| | | | | |
|---|---|---|---|---|
| 5,770,209 | A * | 6/1998 | Grotendorst et al. | 424/198.1 |
| 7,026,299 | B2 * | 4/2006 | Li et al. | 514/44 |
| 7,108,982 | B1 * | 9/2006 | Hageman | 435/7.1 |
| 2003/0180891 | A1 * | 9/2003 | Young et al. | 435/69.4 |
| 2004/0005319 | A1 * | 1/2004 | Grotendorst et al. | 424/145.1 |

FOREIGN PATENT DOCUMENTS

WO WO 01/64946 * 9/2001

OTHER PUBLICATIONS

Opalinska, J. B. et al., Nature Reviews, vol. 1, pp. 503-514 (2002).*
Crooke, S.T., Antisense Research & Application, Chapter 1, pp. 1-50 (Ed. by S. Crooke). Springer-Verlag (1998).*
Chirila, T.V. et al. Biomaterials vol. 23, pp. 321-342 (2002).*
Peracchi, A. Rev. Med. Virol., vol. 14, pp. 47-64 (2004).*
Agrawal, S. et al., Molecular Med. Today, vol. 6, pp. 72-81 (2000).*
Branch, A.D., Trends in Biochem. Sci., vol. 23, pp. 45-50 (1998).*
Yuan, R. et al., Wound Repair & Regeneration, vol. 9, No. 2, p. 154 (Abstract No. 63) (Mar.-Apr. 2001).*
Bai et al. Multivalent Anti-CCR5 Ribozymes for Stem Cell-Based HIV Type 1 Gene Therapy. AIDS Research and Human Retroviruses. 2001, vol. 17, No. 5, pp. 385-399.
Fritz et al. Development of Hammerhead Ribozymes to Modulate Endogenous Gene Expression for Functional Studies. Methods. 2002, vol. 28, pp. 276-285.
Fritz et al. [21] Designating and Characterizing Hammerhead Ribozymes for Use in AAV Vector-Mediated Retinal Gene Therapies. Methods in Enzymology. 2002, vol. 346, pp. 358-377.
Lewin et al. Ribozyme Gene Therapy: Applications for Molecular Medicine. Trends in Molecular Medicine. 2001, vol. 7, No. 5, pp. 221-228.
O'Neill et al. Ribozyme-Based Therapeutic Approaches for Autosomal Dominant Retinitis Pigmentosa. Investigative Ophthalmology & Visual Science. 2000, vol. 41, No. 10, pp. 2863-2869.
Qi et al. Optic Neuropathy Induced by Reductions in Mitochondrial Superoxide Dismutase. Investigative Ophthalmology & Visual Science. 2003, vol. 44, No. 3, pp. 1088-1096.
Qi et al. Suppression of Complex I Gene Expression Induces Optic Neuropathy. Optic Neuropathy. 2003, vol. 53, pp. 198-205.
Ramezani et al. Inhibition of HIV-1 Replication by Retroviral Vectors Expressing Monomeric and Multimeric Hammerhead Ribozymes. Gene Therapy. 1997, vol. 4, pp. 861-867.
Seyhan et al. Ribozyme Inhibition of Alphavirus Replication. The Journal of Biological Chemistry. 2002, vol. 277, No. 29, pp. 25957-25962.
Shaw et al. [49] Ribozymes in Treatment of Inherited Retinal Disease. Methods in Enzymology. 2000, vol. 316, pp. 761-776.
Shen et al. Multi-Ribozyme Targeting of Human Alpha-Globin Gene Expression. Blood Cells, Molecules and Diseases. 1999, vol. 25, No. 24, pp. 361-373.

* cited by examiner

*Primary Examiner*—Jane Zara
(74) *Attorney, Agent, or Firm*—Timothy H. Van Dyke; Beusse Wolter Sanks Mora & Maire

(57) ABSTRACT

Methods and compositions for treating scarring conditions associated with increased expression of connective tissue growth factor (CTGF). Aspects of the invention include ribozymes that cleave mRNA targets required for CTGF expression, cells containing anti-CTGF ribozymes and vectored anti-CTGF ribozymes suitable for delivery to cellular targets capable of CTGF expression.

16 Claims, 11 Drawing Sheets

A

B

A

B

Hammerhead Ribozyme

SEQ ID NO: 58

Self-cleaving Hairpin

SEQ ID NO: 59

SEQUENCE LISTING

```
<160> NUMBER OF SEQ ID NOS: 57

<210> SEQ ID NO 1
<211> LENGTH: 13
<212> TYPE: DNA
<213> ORGANISM: Human adenovirus type 1

<400> SEQUENCE: 1
ggcgcgtccc ggt                                                          13

<210> SEQ ID NO 2
<211> LENGTH: 12
<212> TYPE: DNA
<213> ORGANISM: Human adenovirus type 1

<400> SEQUENCE: 2
ccgcgtcgcc tt                                                           12

<210> SEQ ID NO 3
<211> LENGTH: 12
<212> TYPE: DNA
<213> ORGANISM: Human adenovirus type 1

<400> SEQUENCE: 3
cgtggtcctc ct                                                           12

<210> SEQ ID NO 4
<211> LENGTH: 12
<212> TYPE: DNA
<213> ORGANISM: Human adenovirus type 1

<400> SEQUENCE: 4
ggccgtcggc ca                                                           12

<210> SEQ ID NO 5
<211> LENGTH: 12
<212> TYPE: DNA
<213> ORGANISM: Human adenovirus type 1

<400> SEQUENCE: 5
ccgcgtctgc gc                                                           12

<210> SEQ ID NO 6
<211> LENGTH: 12
<212> TYPE: DNA
<213> ORGANISM: Human adenovirus type 1

<400> SEQUENCE: 6
gagagtcctt cc                                                           12

<210> SEQ ID NO 7
<211> LENGTH: 12
```

```
<210> SEQ ID NO 7
<211> LENGTH: 12
<212> TYPE: DNA
<213> ORGANISM: Human adenovirus type 1

<400> SEQUENCE: 7
gttcgtctgc cc                                                            12

<210> SEQ ID NO 8
<211> LENGTH: 12
<212> TYPE: DNA
<213> ORGANISM: Human adenovirus type 1

<400> SEQUENCE: 8
gagggtcaag ct                                                            12

<210> SEQ ID NO 9
<211> LENGTH: 12
<212> TYPE: DNA
<213> ORGANISM: Human adenovirus type 1

<400> SEQUENCE: 9
cctggtccag ac                                                            12

<210> SEQ ID NO 10
<211> LENGTH: 13
<212> TYPE: DNA
<213> ORGANISM: Human adenovirus type 1

<400> SEQUENCE: 10
gcatggtcag gcc                                                           13

<210> SEQ ID NO 11
<211> LENGTH: 12
<212> TYPE: DNA
<213> ORGANISM: Human adenovirus type 1

<400> SEQUENCE: 11
cgaggtcatg aa                                                            12

<210> SEQ ID NO 12
<211> LENGTH: 11
<212> TYPE: DNA
<213> ORGANISM: Human adenovirus type 1

<400> SEQUENCE: 12
aactgtcccg g                                                             11

<210> SEQ ID NO 13
<211> LENGTH: 12
<212> TYPE: DNA
<213> ORGANISM: Human adenovirus type 1

<400> SEQUENCE: 13
ccacctccga cc                                                            12

<210> SEQ ID NO 14
<211> LENGTH: 12
<212> TYPE: DNA
<213> ORGANISM: Human adenovirus type 1

<400> SEQUENCE: 14
agcgctccag gc                                                            12

<210> SEQ ID NO 15
```

```
<211> LENGTH: 12
<212> TYPE: DNA
<213> ORGANISM: Human adenovirus type 1

<400> SEQUENCE: 15
cgccctccgc tc                                                              12

<210> SEQ ID NO 16
<211> LENGTH: 12
<212> TYPE: DNA
<213> ORGANISM: Human adenovirus type 1

<400> SEQUENCE: 16
tccgctccgc cc                                                              12

<210> SEQ ID NO 17
<211> LENGTH: 12
<212> TYPE: DNA
<213> ORGANISM: Human adenovirus type 1

<400> SEQUENCE: 17
ggtcctcctc gc                                                              12

<210> SEQ ID NO 18
<211> LENGTH: 12
<212> TYPE: DNA
<213> ORGANISM: Human adenovirus type 1

<400> SEQUENCE: 18
cctcctcgcc ct                                                              12

<210> SEQ ID NO 19
<211> LENGTH: 12
<212> TYPE: DNA
<213> ORGANISM: Human adenovirus type 1

<400> SEQUENCE: 19
cgccctctgc ag                                                              12

<210> SEQ ID NO 20
<211> LENGTH: 12
<212> TYPE: DNA
<213> ORGANISM: Human adenovirus type 1

<400> SEQUENCE: 20
gagcctcgtg ct                                                              12

<210> SEQ ID NO 21
<211> LENGTH: 12
<212> TYPE: DNA
<213> ORGANISM: Human adenovirus type 1

<400> SEQUENCE: 21
gggcctcttc tg                                                              12

<210> SEQ ID NO 22
<211> LENGTH: 12
<212> TYPE: DNA
<213> ORGANISM: Human adenovirus type 1

<400> SEQUENCE: 22
ggtgctccct gc                                                              12
```

```
<210> SEQ ID NO 23
<211> LENGTH: 12
<212> TYPE: DNA
<213> ORGANISM: Human adenovirus type 1

<400> SEQUENCE: 23
tgccctcgcg gc                                                            12

<210> SEQ ID NO 24
<211> LENGTH: 12
<212> TYPE: DNA
<213> ORGANISM: Human adenovirus type 1

<400> SEQUENCE: 24
gcatctccac cc                                                            12

<210> SEQ ID NO 25
<211> LENGTH: 12
<212> TYPE: DNA
<213> ORGANISM: Human adenovirus type 1

<400> SEQUENCE: 25
acgcctcctg ca                                                            12

<210> SEQ ID NO 26
<211> LENGTH: 12
<212> TYPE: DNA
<213> ORGANISM: Human adenovirus type 1

<400> SEQUENCE: 26
cgtactccca aa                                                            12

<210> SEQ ID NO 27
<211> LENGTH: 12
<212> TYPE: DNA
<213> ORGANISM: Human adenovirus type 1

<400> SEQUENCE: 27
aaatctccaa gc                                                            12

<210> SEQ ID NO 28
<211> LENGTH: 12
<212> TYPE: DNA
<213> ORGANISM: Human adenovirus type 1

<400> SEQUENCE: 28
cgccttcgtg gt                                                            12

<210> SEQ ID NO 29
<211> LENGTH: 12
<212> TYPE: DNA
<213> ORGANISM: Human adenovirus type 1

<400> SEQUENCE: 29
cctcttctgt ga                                                            12

<210> SEQ ID NO 30
<211> LENGTH: 12
<212> TYPE: DNA
<213> ORGANISM: Human adenovirus type 1

<400> SEQUENCE: 30
tgacttcggc tc                                                            12
```

```
<210> SEQ ID NO 31
<211> LENGTH: 12
<212> TYPE: DNA
<213> ORGANISM: Human adenovirus type 1

<400> SEQUENCE: 31
catcttcggt gg                                                         12

<210> SEQ ID NO 32
<211> LENGTH: 12
<212> TYPE: DNA
<213> ORGANISM: Human adenovirus type 1

<400> SEQUENCE: 32
gtccttccag ag                                                         12

<210> SEQ ID NO 33
<211> LENGTH: 12
<212> TYPE: DNA
<213> ORGANISM: Human adenovirus type 1

<400> SEQUENCE: 33
gacgttcgtc tg                                                         12

<210> SEQ ID NO 34
<211> LENGTH: 12
<212> TYPE: DNA
<213> ORGANISM: Human adenovirus type 1

<400> SEQUENCE: 34 cccctteccg ag                                                         12

<210> SEQ ID NO 35
<211> LENGTH: 12
<212> TYPE: DNA
<213> ORGANISM: Human adenovirus type 1

<400> SEQUENCE: 35
cctgttccaa ga                                                         12

<210> SEQ ID NO 36
<211> LENGTH: 12
<212> TYPE: DNA
<213> ORGANISM: Human adenovirus type 1

<400> SEQUENCE: 36
agctttctgg ct                                                         12

<210> SEQ ID NO 37
<211> LENGTH: 12
<212> TYPE: DNA
<213> ORGANISM: Human adenovirus type 1

<400> SEQUENCE: 37
taaattctgt gg                                                         12

<210> SEQ ID NO 38
<211> LENGTH: 12
<212> TYPE: DNA
<213> ORGANISM: Human adenovirus type 1

<400> SEQUENCE: 38
ggagttcaag tg                                                         12
```

<210> SEQ ID NO 39
<211> LENGTH: 12
<212> TYPE: DNA
<213> ORGANISM: Human adenovirus type 1

<400> SEQUENCE: 39
gatgttcatc aa                                                          12

<210> SEQ ID NO 40
<211> LENGTH: 12
<212> TYPE: DNA
<213> ORGANISM: Human adenovirus type 1

<400> SEQUENCE: 40
caagatcggc gt                                                          12

<210> SEQ ID NO 41
<211> LENGTH: 12
<212> TYPE: DNA
<213> ORGANISM: Human adenovirus type 1

<400> SEQUENCE: 41
ctgcatcttc gg                                                          12

<210> SEQ ID NO 42
<211> LENGTH: 12
<212> TYPE: DNA
<213> ORGANISM: Human adenovirus type 1

<400> SEQUENCE: 42
gggcatctcc ac                                                          12

<210> SEQ ID NO 43
<211> LENGTH: 12
<212> TYPE: DNA
<213> ORGANISM: Human adenovirus type 1

<400> SEQUENCE: 43
gtgcatccgt ac                                                          12

<210> SEQ ID NO 44
<211> LENGTH: 12
<212> TYPE: DNA
<213> ORGANISM: Human adenovirus type 1

<400> SEQUENCE: 44
caaaatctcc aa                                                          12

<210> SEQ ID NO 45
<211> LENGTH: 12
<212> TYPE: DNA
<213> ORGANISM: Human adenovirus type 1

<400> SEQUENCE: 45
gcctatcaag tt                                                          12

<210> SEQ ID NO 46
<211> LENGTH: 12
<212> TYPE: DNA
<213> ORGANISM: Human adenovirus type 1

<400> SEQUENCE: 46

-continued gttcatcaag ac                                                                12

<210> SEQ ID NO 47
<211> LENGTH: 33
<212> TYPE: RNA
<213> ORGANISM: Human adenovirus type 1

<400> SEQUENCE: 47
gucugcugau gaguccuucg ggacgaaacc agg                                          33

<210> SEQ ID NO 48
<211> LENGTH: 33
<212> TYPE: RNA
<213> ORGANISM: Human adenovirus type 1

<400> SEQUENCE: 48
ggccucugau gaguccuucg ggacgaaacc aug                                          33

<210> SEQ ID NO 49
<211> LENGTH: 12
<212> TYPE: RNA
<213> ORGANISM: Human adenovirus type 1

<400> SEQUENCE: 49
ccugguccag ac                                                                12

<210> SEQ ID NO 50
<211> LENGTH: 12
<212> TYPE: RNA
<213> ORGANISM: Human adenovirus type 1

<400> SEQUENCE: 50
cauggucagg cc                                                                12

<210> SEQ ID NO 51
<211> LENGTH: 41
<212> TYPE: DNA
<213> ORGANISM: Human adenovirus type 1

<400> SEQUENCE: 51
agctggcctc tgatgagtcc ttcgggacga aaccatgtgc a                                 41

<210> SEQ ID NO 52
<211> LENGTH: 33
<212> TYPE: DNA
<213> ORGANISM: Human adenovirus type 1

<400> SEQUENCE: 52
catggtttcg tcccgaagga ctcatcagag gcc                                          33

<210> SEQ ID NO 53
<211> LENGTH: 41
<212> TYPE: DNA
<213> ORGANISM: Human adenovirus type 1

<400> SEQUENCE: 53
agctggcctc tcatgagtcc ttcgggacga aaccatgtgc a                                 41

<210> SEQ ID NO 54
<211> LENGTH: 33
<212> TYPE: DNA
<213> ORGANISM: Human adenovirus type 1

<400> SEQUENCE: 54

-continued

```
catggtttcg tcccgaagga ctcatgagag gcc                          33

<210> SEQ ID NO 55
<211> LENGTH: 17
<212> TYPE: DNA
<213> ORGANISM: Human adenovirus type 1

<400> SEQUENCE: 55
agccgcctct gcatggt                                            17

<210> SEQ ID NO 56
<211> LENGTH: 26
<212> TYPE: DNA
<213> ORGANISM: Human adenovirus type 1

<400> SEQUENCE: 56
cacttcttgc ccttcttaat ggttct                                  26

<210> SEQ ID NO 57
<211> LENGTH: 4
<212> TYPE: RNA
<213> ORGANISM: Human adenovirus type 1

<400> SEQUENCE: 57 uucg                                                           4
```

ANTI-SCARRING RIBOZYMES AND METHODS

CROSS REFERENCE TO RELATED APPLICATIONS

The present application claims the priority of U.S. provisional patent application Ser. No. 60/467,119 entitled "Reducing Scar Formation," filed May 1, 2003. The foregoing is incorporated herein by reference in its entirety.

STATEMENT AS TO FEDERALLY FUNDED RESEARCH

This invention was made with U.S. government support under grant number EY05587 awarded by the National Institutes of Health. The U.S. government may have certain rights in the invention.

FIELD OF THE INVENTION

This invention relates generally to the fields of molecular biology and medicine. More particularly, the invention relates to methods and compositions for reduction and prevention of scarring conditions.

BACKGROUND

Scarring, or scar formation, is a reactive condition of connective tissue cells that occurs following surgery and traumatic injury, as well as in fibrosis associated with chronic diseases such as scleroderma. Studies of wound healing and scar formation have shown that several factors are present in elevated levels in fibrotic connective tissue, and in patients with fibrotic diseases such as scleroderma and keloids. Among these is connective tissue growth factor (CTGF), a secreted protein shown to promote the synthesis of extracellular matrix and connective tissue components (Frazier K et al., *J Invest Dermatol* 1996,107(3):404-11; Igarashi A et al., *J Invest Dermatol* 1995,105(2):280-4). Overexpression of CTGF in such conditions may contribute to the observed scarring. Another agent found to be up-regulated in scarring conditions is TGF-$\beta$.

Several anti-scarring drugs have been developed to target TGF-$\beta$, for example by blocking its activation with mannose-6-phosphate analogs, or by neutralizing its action with antibodies.

In the eye, stromal scarring is a major complication following corneal trauma, infection or refractive surgical procedures such as RK. At present, there are no agents that are proven to clinically reduce corneal scarring without causing serious side effects. The use of steroids is prohibited in many instances of infection and has not been shown to be of benefit in controlled studies of PRK. Other agents that have been proposed for clinical use to reduce corneal scarring include drugs such as 5-fluorouracil, mitomycin C, interferon-$\gamma$, cyclosporin A, and a synthetic inhibitor of matrix metalloproteinases. However, powerful, nonspecific anti-cancer drugs can cause serious side effects such as persistent epithelial defects and endothelial damage, and the other drugs have not been tested in clinical trials.

There is a great need to develop agents that selectively inhibit scarring without producing serious side effects.

SUMMARY

The invention relates to the development of ribozymes that can be used to prevent or reduce scarring. In one aspect, the invention includes ribozymes that specifically target and destroy mRNA encoding CTGF, a factor known to be involved in scar formation. More specifically, the invention provides ribozymes that specifically cleave target RNA sequences encoded by CTGF DNA sequences shown as SEQ ID NO's: 1-46. The ribozymes of the invention can be in a hammerhead configuration. The invention includes as preferred embodiments isolated nucleic acids encoding hammerhead ribozymes having nucleic acid sequences shown as SEQ ID NO's :47 and 48, and nucleic acids comprising ribozymes having RNA sequences that are the complement of SEQ ID NO's: 47 and 48.

In a preferred embodiment, expression vectors comprise isolated nucleic acids encoding at least one ribozyme that specifically cleaves target RNA sequences encoded by CTGF nucleotide sequences identified by any one of shown as SEQ ID NO's: 1-46, complements, variants or fragments thereof. Expression vectors including CTGF ribozymes can be used to deliver and synthesize these ribozymes in cells, for the purpose of targeting and destroying RNAs encoding scar-forming CTGF protein.

In certain preferred embodiments, the vectors can include isolated nucleic acids encoding CTGF-targeting hammerhead ribozymes having the nucleotide sequences of SEQ ID NO's: 47 and 48, complements, variants or fragments thereof.

The expression vectors can be in the form of plasmids. In some embodiments, the plasmids comprise isolated nucleic acids that direct the synthesis of a self-cleaving hairpin ribozyme attached to a CTGF ribozyme in a hammerhead configuration. A preferred version of this vector can be based on the plasmid pTRUF21.

The invention further provides a method for reducing CTGF mRNA or protein expression in a cell. The method includes the steps of: (a) providing a tissue containing a cell expressing a target RNA sequence encoded by a CTGF gene; and (b) contacting the tissue with a vector that includes at least one ribozyme that specifically cleaves a target RNA sequence encoded by a CTGF gene, in an amount effective to reduce the CTGF mRNA or protein expression in the cell. The cell can be any cell that expresses CTGF, including fibroblasts.

In a preferred embodiment CTGF mRNA and/or protein expression is reduced by about 20% as compared to the total amount of CTGC mRNA and/or protein expressed by a normal cell, more preferably, CTGF mRNA and/or protein expression is reduced by about 50% as compared to the total amount of CTGC mRNA and/or protein expressed by a normal cell, more preferably, CTGF mRNA and/or protein expression is reduced by about 55%, 60%, 70%, 80%, 85%, 90%, 95%, 99.9% or 100% as compared to the total amount of CTGC mRNA and/or protein expressed by a normal cell.

The method can further include contacting the vector with a tissue in a subject having or at risk for developing a condition causing a scar in that tissue. The condition can be a fibrotic disorder including but not limited to scleroderma, keloids, liver cirrhosis, kidney fibrosis, peritoneal adhesions, tendon adhesions, breast implant capsule adhesions, burn scars, spinal cord injuries, bile duct atresia, subepithelial fibrosis, fibrous dysplasia, and tympanic membrane fibrosis. Other fibrotic conditions can involve wound healing, for example, following surgery. In preferred ocular applications, the surgical procedures can include surgeries of the cornea, (for example, cataract operations, RK) and surgeries of the trabecular meshwork (for example, glaucoma filtering surgery). Ocular tissues to which these vectors can be applied include cornea, conjuctiva, sclera and trabecular meshwork.

In another preferred embodiment, the invention includes a polyzyme that specifically cleaves a target RNA sequence encoded by a CTGF gene, the polyzyme being composed of a plurality of conjoined ribozymes that specifically cleave at least one target RNA sequence encoded by a CTGF nucleotide sequence selected from SEQ ID NO's: 1-46. complements, variants or fragments thereof. In some embodiments, the ribozymes within the polyzyme are separated by G-C rich stem-loop structures.

Unless otherwise defined, all technical terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference for the proposition cited. In the case of conflict, the present specification, including any definitions will control. In addition, the particular embodiments discussed below are illustrative only and not intended to be limiting.

BRIEF DESCRIPTION OF THE DRAWINGS

The invention is pointed out with particularity in the appended claims. The above and further advantages of this invention may be better understood by referring to the following description taken in conjunction with the accompanying drawings, in which:

DETAILED DESCRIPTION

Figure 1:
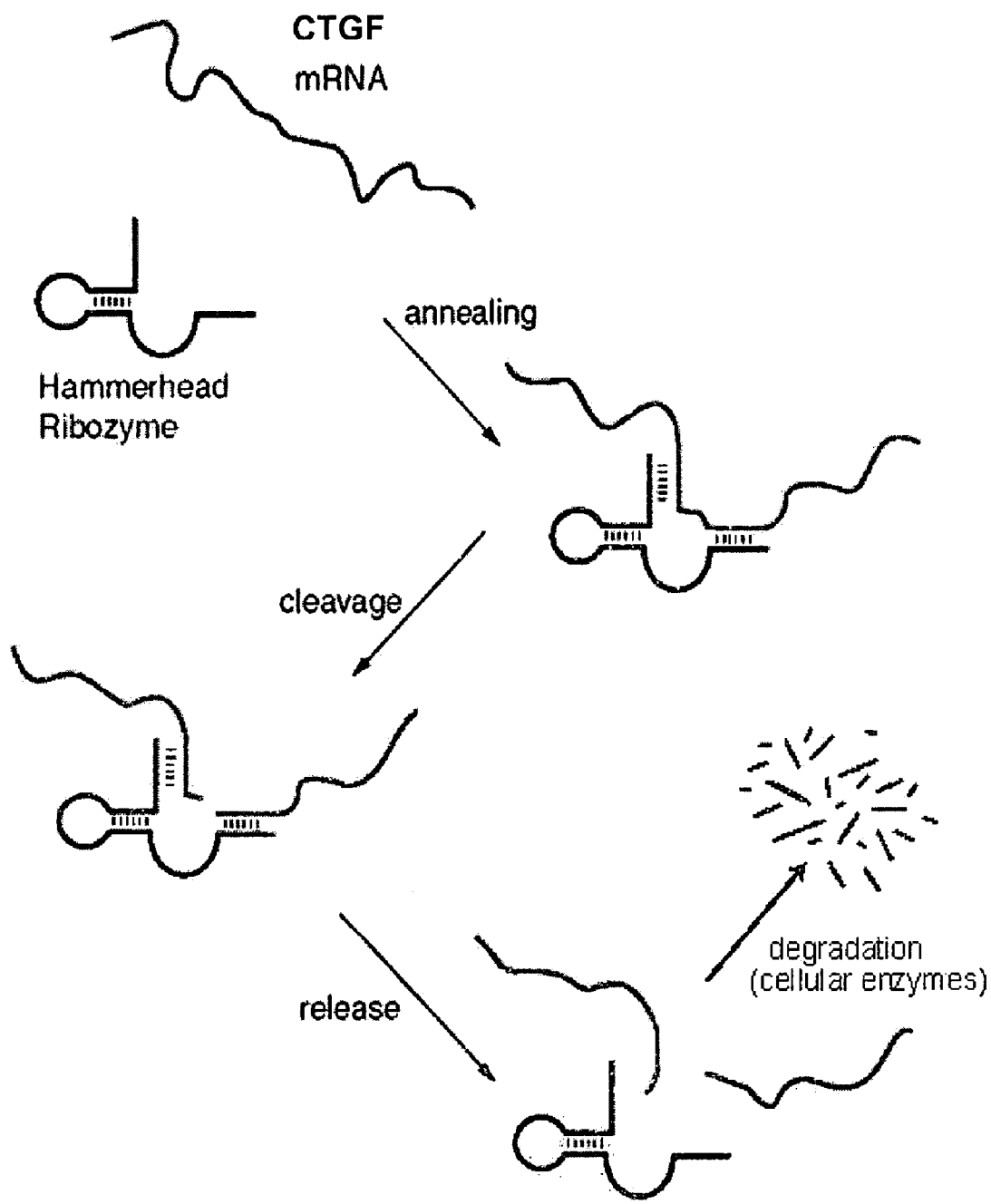
FIG. 1 is a schematic diagram showing the cycle of catalytic cleavage of CTGF mRNA molecules targeted by a ribozyme, according to an embodiment of the invention.

The invention pertains to strategies for reducing scarring using ribozymes, a form of RNA enzyme, that selectively cleave target sequences in mRNA molecules encoding CTGF. Cleavage of the CTGF mRNA by such ribozymes prevents or greatly impairs the ability of cells to express CTGF mRNA needed for production of CTGF protein, a secreted factor with known involvement in the scarring process (Igarashi A et al., *J. Invest Dermatol* 106: 729-733, 1996; Grotendorst G R, *Cytokine Growth Factor Rev* 8:171-179, 1997). In one aspect, the invention provides CTGF-targeting ribozymes that specifically cleave target RNA sequences encoded by CTGF genes. Also provided are expression vectors including nucleic acid sequences encoding ribozymes directed against target sequences in CTGF mRNA molecules. In another aspect, the invention includes cells transduced with vectors that direct expression of CTGF-targeting ribozymes in the cells. In yet a further embodiment, methods are provided for using the vectors to reduce CTGF mRNA and protein synthesis and protein secretion, for example in cells such as dermal and corneal fibroblasts, which contribute significantly to the scarring response during wound healing and in fibrotic disorders.

Prior to setting forth the invention in detail, the following definitions if appearing herein, are provided:

A "vector" is a replicon, such as plasmid, phage or cosmid, to which another DNA segment may be attached so as to bring about the replication of the attached segment.

A "replicon" is any genetic element (e.g., plasmid, chromosome, virus) that functions as an autonomous unit of DNA replication in vivo, i.e., capable of replication under its own control.

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

A cell has been "transfected" by exogenous or heterologous DNA when such DNA has been introduced inside the cell. A cell has been "transformed" by exogenous or heterologous DNA when the transfected DNA effects a phenotypic change.

"Heterologous" DNA refers to DNA not naturally located in the cell, or in a chromosomal site of the cell. Preferably, the heterologous DNA includes a gene foreign to the cell.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the MRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ of 55° C., can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50-0.51). For hybridization with shorter nucleic acids, i.e., oligonucleotides, the position of mismatches becomes more important, and the length of the oligonucleotide determines its specificity (see Sambrook et al., supra, 11.7-11.8). Preferably a minimum length for a hybridizable nucleic acid is at least about 12 nucleotides; preferably at least about 18 nucleotides: and more preferably the length is at least about 27 nucleotides; and most preferably about 36 nucleotides.

"Homologous recombination" refers to the insertion of a foreign DNA sequence of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic MRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For example, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced and translated into the protein encoded by the coding sequence.

As used herein, the term "sequence homology" in all its grammatical forms refers to the relationship between proteins that possess a "common evolutionary origin," including proteins from superfanilies (e.g., the immunoglobulin superfamily) and homologous proteins from different species (e.g., myosin light chain, etc.) [Reeck et al., Cell, 50:667 (1987)].

Accordingly, the term "sequence similarity" in all its grammatical forms refers to the degree of identity or correspondence between nucleic acid or amino acid sequences of proteins that do not share a common evolutionary origin [see Reeck et al., 1987, supra]. However, in common usage and in the instant application, the term "homologous," when modified with an adverb such as "highly," may refer to sequence similarity and not a common evolutionary origin.

Two DNA sequences are "substantially homologous" or "substantially similar" when at least about 50% (preferably at least about 75%, and most preferably at least about 90%, 95% or 99.9%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

Similarly, two amino acid sequences are "substantially homologous" or "substantially similar" when greater than 30% of the amino acids are identical, or greater than about 60% are similar (functionally identical). Preferably, the similar or homologous sequences are identified by alignment using, for example, the GCG (Genetics Computer Group, Program Manual for the GCG Package, Version 7, Madison, Wis.) pileup program.

The term "corresponding to" is used herein to refer similar or homologous sequences, whether the exact position is identical or different from the molecule to which the similarity or homology is measured. Thus, the term "corresponding to" refers to the sequence similarity, and not the numbering of the amino acid residues or nucleotide bases.

As used herein, linkage describes the tendency of genes, alleles, loci or genetic markers to be inherited together as a result of their location on the same chromosome. It can be measured by percent recombination between the two genes, alleles, loci or genetic markers.

As used herein, "polymorphism" or "variants" refers to the occurrence of two or more genetically determined alternative sequences or alleles in a population. A polymorphic marker or site is the locus at which divergence occurs. Preferred markers have at least two alleles, each occurring at frequency of greater than 1%, and more preferably greater than 10% or 20% of a selected population. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wildtype form. Diploid organisms may be homozygous or heterozygous for allelic forms. A diallelic or biallelic polymorphism has two forms. A triallelic polymorphism has three forms.

CTGF-Targeting Ribozymes

The invention provides in one aspect a ribozyme that specifically cleaves a target RNA sequence encoded by a CTGF gene. Any mRNA sequence encoded by a CTGF gene and cleavable by a ribozyme can be targeted by the ribozymes of the invention. Several forms of naturally-occurring and synthetic ribozymes are known, including Group I and Group II introns, RNaseP, hairpin ribozymes and hammerhead ribozymes (Lewin AS and Hauswirth WW, Trends in Molecular Medicine 7: 221-228, 2001).

Hammerhead Ribozymes Targeting CTGF mRNAs

The ribozymes of the invention can be in a hammerhead configuration. Hammerhead ribozymes may be advantageous because, as shown in the examples below, they have proven to be highly effective at cleaving target RNA sequences selective for CTGF genes. In general, ribozymes catalyze site-specific cleavage or ligation of phosphodiester bonds in RNA. Hammerhead and hairpin ribozymes are RNA molecules that act as enzymes by base pairing with complementary RNA target sequences, and carrying out cleavage reactions at particular sites. As depicted in FIG. 1, synthetic hammerhead ribozymes can be engineered to selectively bind and cleave a complementary mRNA molecule and then release the fragments, repeating the process with the efficiency of a protein enzyme. This represents a significant advantage over other RNA-based inhibitors, for example, antisense oligonucleotides, which are stoichiometric as opposed to catalytic in their mechanism of action, and thus are limited to forming a 1:1 complex with their target sequence.

In the case of the hammerhead ribozyme, the RNA enzyme cleaves after UX dinucleotides, where X can be any ribonucleotide except guanosine, although the rate of cleavage is highest if X is cytosine. The catalytic efficiency is further affected by the nucleotide preceding the uridine. In practice, NUX triplets (typically GUC, CUC or UUC) are required in the target mRNA. Such targets are used to design an antisense RNA of 12 or 13 nucleotides surrounding that site, but skipping the C, which does not form a conventional base pair with the ribozyme.

Figure 2:
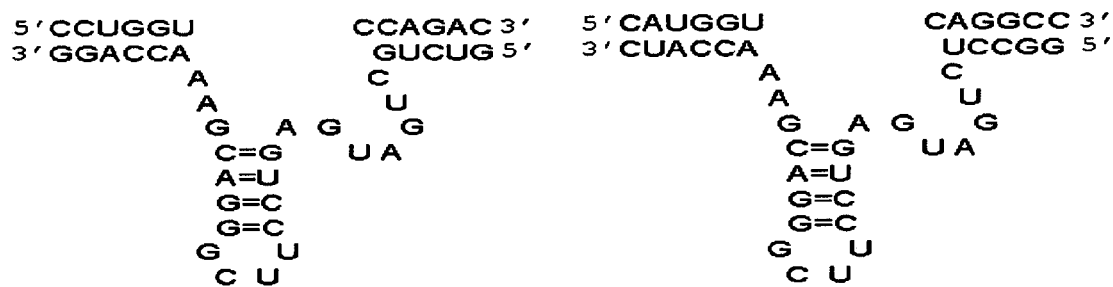
FIG. 2 is a schematic diagram showing the RNA sequences of two 33 mer CTGF hammerhead ribozymes (i.e., ribozyme CHR 745, left and CHR 859, right), according to an embodiment of the invention. Corresponding 12 mer target RNA sequences in CTGF mRNA are shown aligned with the ribozymes.

FIG. 2 shows examples of the design of several hammerhead ribozymes according to the invention, aligned with the hammerhead portions of the molecules facing their respective RNA targets. In the embodiments shown in FIG. 2, the ribozymes are designed in a 6-4-5 stem-loop-stem configuration. Any other configuration suitable for the purpose can be used. In general, because the chemical cleavage step is rapid and the release step is rate-limiting, speed and specificity are enhanced if the hybridizing "arms" of the ribozyme (helices I and III) are relatively short, for example, about 5 or 6 nucleotides. Suitability of the design of a particular configuration can be determined empirically, using various assays as described below.

In various embodiments of the hammerhead ribozymes of the invention, the nucleotide sequences of the portions of the CTGF gene (i.e., cDNA) corresponding to the RNA-targeting "hammerhead" portions of the ribozymes can be as listed in Table 1. CTGF sequences listed in Table 1 are identified herein as SEQ ID NO's: 1-46, complements, variants or fragments thereof. Referring to FIG. 2, it can be appreciated that the RNA-targeting portion (i.e., the "arm") of a ribozyme is complementary to its RNA target, and therefore is encoded by DNA having the same sequence as the target RNA, except for the replacement of thymidine (T) with uridine (U).

TABLE 1

DNA Sequences Encoding RNA Targets of the CTGF Gene

| | | | | | |
|---|---|---|---|---|---|
| SEQ. ID NO: | 1 | CTGF | 46-59 | ggcgcgtcccggt |
| SEQ. ID NO: | 2 | CTGF | 172-183 | ccgcgtcgccttt |
| SEQ. ID NO: | 3 | CTGF | 184-195 | cgtggtcctcct |
| SEQ. ID NO: | 4 | CTGF | 214-225 | ggccgtcggcca |
| SEQ. ID NO: | 5 | CTGF | 316-327 | ccgcgtctgcgc |
| SEQ. ID NO: | 6 | CTGF | 483-494 | gagagtccttcc |
| SEQ. ID NO: | 7 | CTGF | 566-577 | gttcgtctgccc |
| SEQ. ID NO: | 8 | CTGF | 601-612 | gagggtcaagct |
| SEQ. ID NO: | 9 | CTGF | 742-753 | cctggtccagac |

TABLE 1-continued

DNA Sequences Encoding RNA Targets of the CTGF Gene

| SEQ ID NO: | Gene | Position | Sequence |
|---|---|---|---|
| SEQ. ID NO: 10 | CTGF | 855-867 | gcatggtcaggcc |
| SEQ. ID NO: 11 | CTGF | 1075-1086 | cgaggtcatgaa |
| SEQ. ID NO: 12 | CTGF | 1127-1137 | aactgtcccgg |
| SEQ. ID NO: 13 | CTGF | 61-72 | ccacctccgacc |
| SEQ. ID NO: 14 | CTGF | 79-90 | agcgctccaggc |
| SEQ. ID NO: 15 | CTGF | 117-128 | cgccctccgctc |
| SEQ. ID NO: 16 | CTGF | 122-133 | tccgctccgccc |
| SEQ. ID NO: 17 | CTGF | 187-198 | ggtcctcctcgc |
| SEQ. ID NO: 18 | CTGF | 190-201 | cctcctcgccct |
| SEQ. ID NO: 19 | CTGF | 196-207 | cgccctctgcag |
| SEQ. ID NO: 20 | CTGF | 286-297 | gagcctcgtgct |
| SEQ. ID NO: 21 | CTGF | 379-390 | gggcctcttctg |
| SEQ. ID NO: 22 | CTGF | 443-454 | ggtgctccctgc |
| SEQ. ID NO: 23 | CTGF | 676-687 | tgccctcgcggc |
| SEQ. ID NO: 24 | CTGF | 792-803 | gcatctccaccc |
| SEQ. ID NO: 25 | CTGF | 819-830 | acgcctcctgca |
| SEQ. ID NO: 26 | CTGF | 917-928 | cgtactcccaaa |
| SEQ. ID NO: 27 | CTGF | 927-938 | aaatctccaagc |
| SEQ. ID NO: 28 | CTGF | 178-189 | cgccttcgtggt |
| SEQ. ID NO: 29 | CTGF | 382-393 | cctcttctgtga |
| SEQ. ID NO: 30 | CTGF | 391-402 | tgacttcggctc |
| SEQ. ID NO: 31 | CTGF | 454-465 | catcttcggtgg |
| SEQ. ID NO: 32 | CTGF | 487-498 | gtccttccagag |
| SEQ. ID NO: 33 | CTGF | 563-574 | gacgttcgtctg |
| SEQ. ID NO: 34 | CTGF | 589-600 | ccccttcccgag |
| SEQ. ID NO: 35 | CTGF | 768-779 | cctgttccaaga |
| SEQ. ID NO: 36 | CTGF | 951-962 | agctttctggct |
| SEQ. ID NO: 37 | CTGF | 988-999 | taaattctgtgg |
| SEQ. ID NO: 38 | CTGF | 1054-1065 | ggagttcaagtg |
| SEQ. ID NO: 39 | CTGF | 1096-1107 | gatgttcatcaa |
| SEQ. ID NO: 40 | CTGF | 415-426 | caagatcggcgt |
| SEQ. ID NO: 41 | CTGF | 451-462 | ctgcatcttcgg |
| SEQ. ID NO: 42 | CTGF | 790-801 | gggcatctccac |
| SEQ. ID NO: 43 | CTGF | 910-921 | gtgcatccgtac |
| SEQ. ID NO: 44 | CTGF | 925-936 | caaaatctccaa |
| SEQ. ID NO: 45 | CTGF | 937-948 | gcctatcaagtt |
| SEQ. ID NO: 46 | CTGF | 1099-1110 | gttcatcaagac |

The invention further includes an isolated nucleic acid encoding a hammerhead ribozyme that specifically cleaves a target RNA sequence encoded by a CTGF gene, wherein the ribonucleic acid sequence of the ribozyme is the sequence of SEQ ID NO's: 47 or 48, as shown:

```
(SEQ ID NO: 47)
5'-GUCUGCUGAUGAGUCCUUCGGGACGAAACCAGG-3';

(SEQ ID NO: 48)
5'-GGCCUCUGAUGAGUCCUUCGGGACGAAACCAUG-3'.
```

FIG. 2 shows a schematic of the structure of these particular embodiments of the inventive hammerhead ribozymes. These embodiments are preferred as they are highly efficient at cleaving CTGF message in kinetic studies, and following transfection and expression in human fibroblasts.

In this regard, secondary structure in RNA is known to be relatively stable and can interfere with the ability of a ribozyme to bind to its target site. For this reason, some synthetic ribozymes are found to be more efficient than others at cleaving their RNA targets. Structure-predicting algorithms such as MFOLD can be used to rule out certain target sites, but ultimately accessibility can be determined experimentally.

To determine the cutting efficiency of a particular ribozyme, a series of in vitro tests can be used for prediction of in vivo behavior of designed synthetic ribozymes (Shaw et al., *Methods Enzymol.* 316:761-776, 2000; Fritz J J et al., *Methods Enzymol.* 346:358-377, 2002). In vitro screening of the kinetic properties of hammerhead ribozymes is recognized to be a cost-efficient analytic step, enabling selection of ribozymes having optimal cleavage characteristics without the necessity of more expensive animal studies. The examples below provide further details of screening methods useful for determining efficacy of the ribozymes of the invention, including assays of activity and multiple turnover kinetic analysis using short RNA targets and full length targets. Also described are assays using cells transfected with vectors directing cellular synthesis of the CTGF-targeting ribozymes of the invention, to determine the ability of the ribozymes to reduce endogenous CTGF mRNA and protein expression, and CTGF secretion by the transfected cells.

Vectors Expressing CTGF-Targeting Ribozymes

Also within the invention are vectors including an isolated nucleic acid encoding at least one ribozyme that specifically cleaves target RNA sequences encoded by the CTGF gene. (Deposited with ATCC Apr. 29, 2004). In preferred embodiments, the CTGF targets are within the human CTGF gene, and are encoded by the nucleotide sequences indicated as SEQ ID NO's: 1-46.

Nucleic acids encoding the ribozymes of the invention can be incorporated into recombinant nucleic acid constructs, typically DNA constructs, capable of introduction into and replication in a host cell. Such a construct preferably is a vector that includes a replication system and sequences that are capable of transcription in a given host cell. For the present invention, conventional compositions and methods for preparing and using vectors and host cells can be employed, as described, for example, in Sambrook et al., supra, or Ausubel et al., supra.

An "expression vector" is a vector capable of expressing a DNA (or cDNA) molecule cloned into the vector and, in certain cases, producing an RNA or a polypeptide or protein. Appropriate transcriptional and/or translational control sequences are included in the vector to allow it to be expressed in a cell. Expression of the cloned sequences occurs when the expression vector is introduced into an appropriate host cell. If a eukaryotic expression vector is employed, then an appropriate host cell would be any eukaryotic cell capable of expressing the cloned sequences. As described below, in preferred embodiments of the invention, fibroblasts, for example, human dermal and corneal fibroblasts, are appropriate host cells.

A number of expression vectors suitable for stable transformation of animal cells are known. See, for example, Pouwels et al., Cloning Vectors: A Laboratory Manual, 1985, Supp. 1987. Typically, animal expression vectors include (1) one or more cloned animal genes under the transcriptional control of 5' and 3' regulatory sequences and (2) a dominant selectable marker. Such animal expression vectors may also contain, if desired, a promoter regulatory region (for example, a regulatory region controlling expression that is inducible or constitutive, environmentally- or developmentally-regulated, or cell- or tissue-specific), a transcription initiation start site, a ribosome binding site, an RNA processing signal, a transcription termination site, and/or a polyadenylation signal.

An example of a useful promoter which could be used to express a ribozyme according to the invention is a chicken β-actin promoter. These promoters confer high levels of expression in most animal tissues, and are generally not dependent on the particular encoded messages to be expressed. As described below, the chicken β-actin promoter with a cytomegalovirus (CMV) enhancer was found to be effective in driving synthesis of ribozymes targeting CTGF mRNA sequences. Other promoters that may be useful in the invention can include the Rous sarcoma virus promoter, adenovirus major late promoter (MLP), herpes simplex virus (HSV) promoter, HIV long terminal repeat (LTR) promoter, mouse mammary tumor virus LTR promoter, or the murine metallothionein promoter (Stratagene San Diego Calif.). Synthetic promoters, hybrid promoters, and the like are also useful in the invention and are known in the art.

Animal expression vectors within the invention preferably contain a selectable marker gene used to identify cells that have become transformed. Suitable selectable marker genes for animal systems include genes encoding enzymes that produce antibiotic resistance (for example, those conferring resistance to hygromycin, kanamycin, bleomycin, neomycin, and streptomycin).

Vectors shown to be useful in the successful transduction of human fibroblasts, leading to synthesis of CTGF-targeting ribozymes by the transduced cells, are described in the examples below. In preferred embodiments, the vectors of the invention can be plasmid vectors. The plasmid pTRUF21HP can be especially useful for the production of ribozymes by cells, in that this vector includes sequences that direct synthesis of self-cleaving hairpin ribozymes attached to CTGF-targeting hammerhead ribozymes. Upon expression in a cell, the hairpin ribozyme self-cleaves, increasing the bioavailability of the hammerhead CTGF-targeting ribozyme. This plasmid also contains 145 nucleotide inverted repeat sequences sufficient for packaging the DNA sequences between them in recombinant Adeno-associated Virus (rAAV). In a preferred embodiment, rAAV can be used to transfer the desired genes to the target cells at the site of surgery or injury, for example in the cornea or the trabecular meshwork. Other methods, including naked DNA, other viral vectors or liposomes can also be used to deliver the ribozymes to the desired location.

Advantages of using rAAV relative to other viral vectors is its lack of pathogenicity, its ability to infect a wide variety of cell types and its ability to infect growth-arrested cells. Unlike retroviruses, long term genetic transduction by AAV does not appear to involve integration of vector DNA into the host chromosome, thus minimizing the possibility of insertional mutagenesis. Recombinant AAV lacking its normal rep and cap genes is currently used for gene transfer to a variety of tissues. It is possible to produce high titers ($10^{14}$ particles per milliliter) of pure virus in tissue culture. Even though more than 80% of the population has been exposed to AAV, this virus has not been associated with disease, making it inherently safer than adenovirus, herpesvirus or lentivirus as a means for gene delivery.

Method For Reducing CTGF Expression in a Cell

The invention further encompasses the use of ribozyme vectors to reduce or inhibit CTGF mRNA or protein expression and secretion in cells. This is accomplished by incorporating nucleic acids encoding ribozymes directed against CTGF mRNA targets into vectors, and delivering these vectors to cells capable of expressing CTGF mRNA.

Accordingly, the invention features a method for reducing CTGF mRNA or protein expression in a cell. The method includes the steps of: (a) providing a tissue including a cell expressing a target RNA sequence encoded by a CTGF gene; and (b) contacting the tissue with a vector including a nucleic acid that encodes at least one ribozyme that specifically cleaves a target RNA sequence encoded by a CTGF gene, in an amount effective to reduce the CTGF or protein expression in the cell.

The cell can be any cell capable of expression of CTGF. Cell types particularly suitable for treatment with the CTGF-targeting ribozyme vectors of the invention are cells of connective tissues involved in the process of scar formation. Prominent among these are fibroblasts, which are responsible for the synthesis of collagen and other extracellular matrix components. For ocular applications, preferred ocular tissues, which contain abundant fibroblasts and epithelial cells and are susceptible to scarring, include the cornea, conjunctiva, sclera, and the trabecular meshwork in the anterior chamber of the eye.

Treatment Methods for Scarring Disorders

The above-described method of the invention can further be applied to a tissue in a subject having or at risk for developing a condition causing a scar in the tissue. Conditions suitable for treatment with the method can be any form of fibrotic disorder in which expression of CTGF is expected to result in or exacerbate scar formation. Conditions suitable for treatment with the methods of the invention include but are not limited to liver cirrhosis, kidney fibrosis, peritoneal adhesions, tendon adhesions, breast implant capsules, burn scars, spinal cord injuries, bile duct atresia, and tympanic membrane fibrosis.

Suitable subjects for use in the invention can be any animal. For example, the subject can be an animal such as mammal like a dog, cat, horse, cow, pig, sheep, goat, chicken, primate, rat, mouse or human. Preferred are subjects suspected of having, or at risk for developing, a scarring condition or disorder, for example, a person suspected of having, or at risk for developing, any form of fibrotic disorder, based on clinical findings or other diagnostic test results.

Other suitable human subjects include patients at risk for developing scars due to wound healing, including wounds resulting from surgical procedures. Ocular surgical procedures for which the method may be particularly suitable include corneal surgeries, such as RK, PRK and LASIK, and surgical interventions, such as trabeculectomy, for ocular drainage in glaucoma conditions.

The method may be performed in a subject by introducing into the subject's tissue (containing cells expressing CTGF) a composition including an expression vector of the invention including a nucleic acid encoding at least one ribozyme that specifically cleaves a target RNA sequence encoded by a CTGF gene, in an amount effective to reduce the CTGF mRNA or protein expression in the cells. In preferred embodiments, the CTGF is human CTGF.

Administration of Compositions

The compositions of the invention can be administered to animals or humans by any conventional technique. Such administration might be parenteral (for example, intravenous, subcutaneous, intramuscular, or intraperitoneal introduction). Preferably, the compositions may be administered directly to the target site (for example, to the eye, or to a compartment of the eye, such as the cornea or trabecular meshwork), such as by direct application, as in the form of an eye drop.

An effective amount of CTGF-targeting ribozyme vector sufficient for reducing or eliminating the scarring disease or condition can be determined by established procedures for evaluation of outcomes of gene therapy procedures. In general, determination of an effective amount of the composition is made in the subject before and after administration of the compositions, using standard methods known in the art, such as measurements of indicia and rates of healing and scar formation at the site of injury or surgery. For animal subjects, many suitable models are available for following the course of scar formation after various forms of wounding. For example, evaluation of the effects of expressed CTGF-targeting ribozymes on corneal wound healing can be performed in a rat model of corneal scarring created by bilateral PRK ablation (Chen C et al., *Invest Ophthalmol Vis Sci* 2000, 41:4108-4116). At various intervals following administration of test compositions (such as plasmid expressing active ribozyme, plasmid expressing inactive ribozyme, or vehicle alone), typical parameters for analysis can include: 1) degree of corneal haze, determined by slit lamp biomicroscopy; 2) histological features and immunohistochemical staining patterns, determined in excised eyes (for example, new collagen formation, and expression of specific types of collagen, such as types I, III, and IV); and 3) levels of expression of CTGF mRNA and protein, determined using standard biochemical and molecular biological methods as described herein.

Determination of an effective amount of vector for gene transfer to a human subject is guided by results from animal studies. Outcomes in human patients are monitored in controlled studies using standardized clinical protocols, and appropriate measurement techniques (such as, in the eye, funduscopy, fluorescein angiography, indocyanine green angiography, and the like) known to specialists experienced in the management of patients with such disorders.

EXAMPLES

The following examples serve to illustrate the invention without limiting it thereby. It will be understood that variations and modifications can be made without departing from the spirit and scope of the invention.

Example 1

Ribozyme Design and Synthesis

Potential ribozyme target sites within the human CTGF cDNA sequence were initially selected based on identification of the single-stranded regions. (See Table 1, supra.) Two targets, designated CHR 745 and CHR 859, containing the highest A and U content, were selected for subsequent analysis. Corresponding 33 mer RNAs containing a hammerhead ribozyme and 12 mer RNA targets were chemically synthesized and 2'-ACE protected (Dharnacon Research Inc.; Lafayette, Colo.).

Referring to FIG. 2, the ribonucleotide sequence of the synthetic ribozyme designed to target the CHR 745 substrate RNA is as follows:
5'-GUCUGCUGAUGAGUCCUUCGGGAC-GAAACCAGG-3' (SEQ ID NO:47). As can be seen in the figure, the sequence of a synthetic 12 mer RNA target oligonucleotide for CHR 745 is the following:
5'-CCUGGUCCAGAC-3' (SEQ ID NO:49).

As shown on the right in FIG. 2, the sequence of the ribozyme designed to target the CHR 859 substrate RNA is:
5'-GGCCUCUGAUGAGUCCUUCGGGAC-GAAACCAUG-3' (SEQ ID NO:48). The sequence of the 12 mer RNA target oligonucleotide for CHR 859 is the following:
5'-CAUGGUCAGGCC-3' (SEQ ID NO:50).

Example 2

Ribozyme Time Course and Multi-turnover Kinetics

Target oligonucleotide RNAs were de-protected according to the manufacturer's directions and labeled with $\gamma$-$^{32}$P-dATP using the following reaction: 2 µl oligo-RNA (10 pmol/µl), 1 µl Rnasin (Promega; Madison, Wis), 1 µl 0.1M DTT, 3 µl ddH$_2$O, 1 µ$\gamma^{32}$P-dATP, 1 µl 10×PNK buffer, and 1 µl T4 polynucleotide kinase (Roche Molecular Biochemicals; Indianapolis, Ind.). Chemically synthesized RNA was labeled by [γ³²P]-ATP using polynucleotide kinase (PNK). Polynucleotide kinase catalyzes the transfer of the terminal phosphate of ATP to the 5'-hydroxyl terminus of ribo- and deoxyribonucleotides. The reaction was incubated at 37° C. for 30 minutes, and then diluted to 100 µl with double distilled water, followed by extraction with phenol/chloroform/isoamyl alcohol (25:24: 1). Free nucleotides were removed by passing the aqueous layer on a Sephadex G25 fine spin column. RNA was ethanol precipitated and resuspended in 100 µl ddH₂O to a final concentration of 0.2 pmol/µl.

Ribozyme cleavage reactions were performed in the presence or absence of various concentrations of ribozyme and target RNA in a reaction mix (20 µl) containing 40 mM Tris/HCl, pH=7.5 and 20 mM MgCl₂. Samples were incubated at 37° C. and the reaction was initiated by addition of ribozyme to target RNA. At selected times, the reactions were arrested with the addition of a 6 µL of 90% formamide, 50 mM EDTA (pH=8.0), 0.05% xylene cyanol, and 0.05% bromophenol blue. Reaction products were separated on a 19% polyacrylamide gel containing 8 M urea, and were quantitated by radioanalytic scanning (PhosphorImager; Molecular Dynamics, Durham, N.C.).

In the time course study, reaction mixtures included 10 pmol ribozyme and 100 pmol target RNA (containing 0.2 pmol γ-³²P-target). Reactions were stopped at 0.5 min, 1 min, 2 min, 3 min, 4 min, 5 min, 10 min, 30 min, 1 hr, 2 hr, 3 hr and 15 hr. In the multi-turnover study, reactions were stopped at 1 min. Reactions included 0.015 pmol/µL of ribozyme and increasing concentrations of target RNA (0.15-15 pmol/µL), as indicated in Table 2.

TABLE 2

Variable concentrations of target RNA and constant concentrations of ribozyme RNA used in multi-turnover kinetics analysis.

|  | 1 | 2 | 3 | 4 | 5 | 6 | 7 | 8 | 9 | 10 | 11 | 12 |
|---|---|---|---|---|---|---|---|---|---|---|---|---|
| Ribozyme | 0 | 0.015 | 0.015 | 0.015 | 0.015 | 0.015 | 0.015 | 0.015 | 0.015 | 0.015 | 0.015 | 0.015 |
| Target | 0.15 | 0.15 | 0.3 | 0.6 | 0.9 | 1.2 | 1.5 | 3.0 | 6.0 | 9.0 | 12 | 15 |

Plots of substrate concentration over velocity versus substrate concentration were used to determine values for maximum velocity (Vmax), Michaelis-Menten constant (Km), and reaction rate at saturating substrate concentration (Kcat).

Example 3

Kinetics of CTGF Hammerhead Ribozymes

Time course and multi-turnover studies as described above were performed to test the kinetic properties of the CHR 745 and CHR 859 ribozymes. Two products were produced following cleavage of the labeled synthetic products by the ribozyme: a 7-nucleotide 5' product and a 5-nucleotide 3' product. The intact oligo-RNA and 5' product, labeled by γ³²P-ATP, were detectable by radioanalytic scanning.

Figure 3:
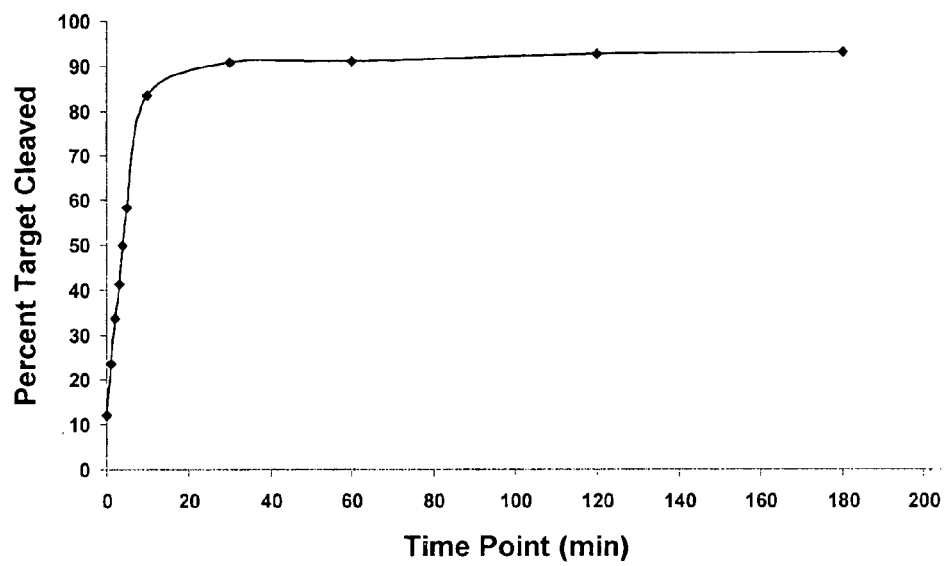
FIG. 3 is two graphs showing the time course of CTGF target RNA cleavage by ribozymes CHR 859 (A) and CHR 745 (B), according to an embodiment of the invention.
Figure 3:
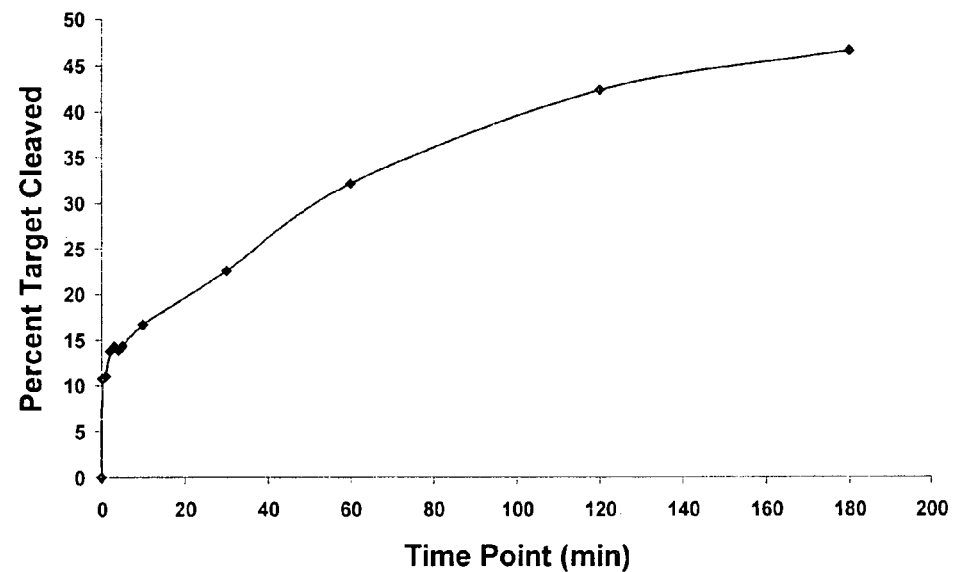

Referring to FIG. 3, ribozyme CHR 859 (FIG. 3A) was significantly more active in time course studies than ribozyme CHR 745 (FIG. 3B), cleaving 92% vs. 22% of the target RNA substrate at 30 minutes, and 94% compared with 46% at the end of incubation. Data shown in FIG. 3 are the result of two experiments.

Figure 4:
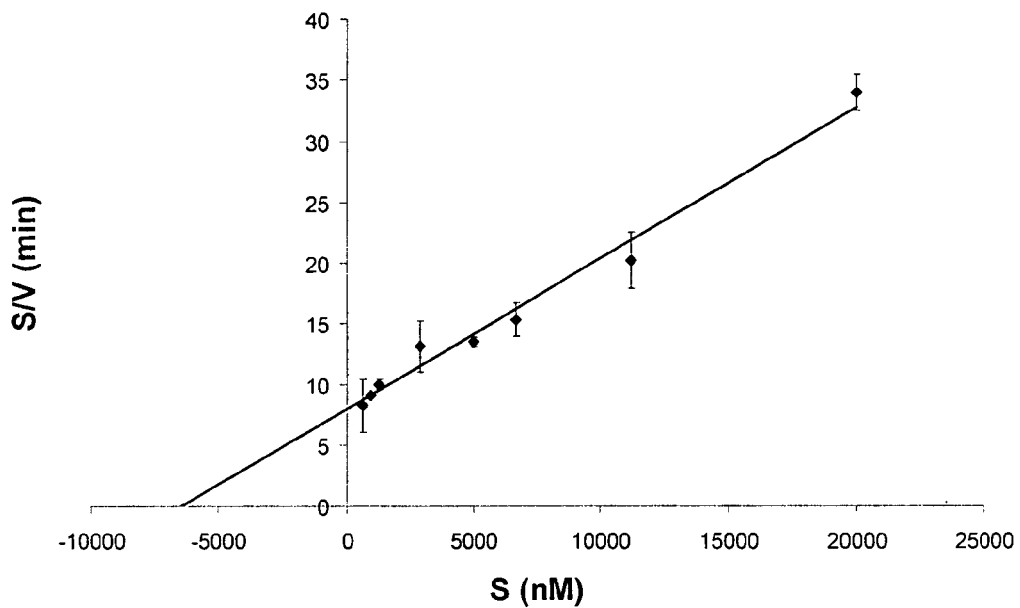
FIG. 4 is two graphs from multi-turnover kinetic analyses of ribozymes CHR 859 (A) and CHR 745 (B), according to an embodiment of the invention. Haynes-Wolff plots are shown indicating Michaelis-Menten kinetics. The duration of the cleavage reactions was one minute.
Figure 4:
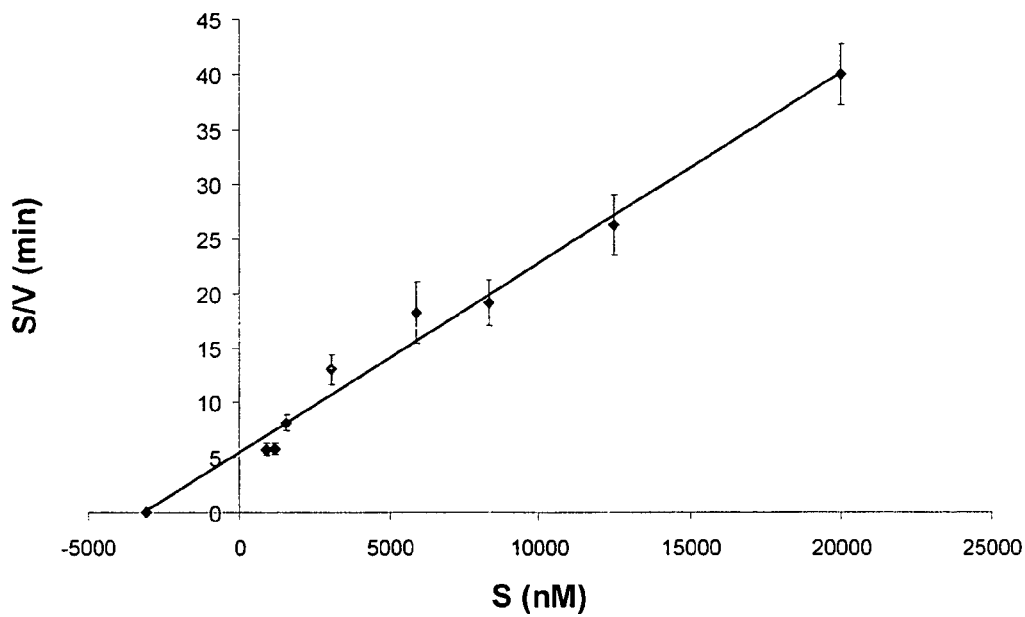

Catalytic efficiency of these ribozymes was estimated by measuring steady-state cleavage velocities with constant amounts (15 pM) of ribozyme and increasing concentrations (150-15,000 pM) of the substrate. As shown in FIG. 4, the enzymatic reactions demonstrated Michaelis-Menten kinetics and were analyzed using Haynes-Wolff plots. Ribozyme CHR 859 (FIG. 4A) showed a $K_m$ of 1.56 µM and a $K_{cat}$ of 2.97/min, whereas CHR 745 (FIG. 4B) had a $K_m$ of 7.80 µM and a $K_{cat}$ of 5.7/min. The turnover numbers (Kcat/Km) of CHR 859 and CHR 745 were $1.9 \times 10^6$ M/min and $7.4 \times 10^5$ M/min, respectively. Thus, ribozyme CHR 859 was 2.6 times more efficient than ribozyme CHR 745.

Example 4

Construction of Ribozyme Plasmids

Single-stranded synthetic DNA oligonucleotides encoding ribozyme CHR 745 were chemically synthesized. The synthesized sequences were as follows:

```
CHR 745 sense:                              (SEQ ID NO:51)
5'-AGCTGGCCTCTGATGAGTCCTTCGGGACGAAACCATGTGCA-3'

CHR 745 antisense:                          (SEQ ID NO:52)
5'-CATGGTTTCGTCCCGAAGGACTCATCAGAGGCC.
```

To create a control ribozyme that is inactive, a second pair of oligonucleotides was constructed by replacing the above-indicated underlined nucleotides (G to C; C to G). Accordingly, the oligonucleotide sequences of the inactive control ribozymes are as follows:

```
CHR 745 sense:                              (SEQ ID NO:53)
5'-AGCTGGCCTCTCATGAGTCCTTCGGGACGAAACCATGTGCA-3'
```

CHR 745 antisense: 5'-CATGGTTTCGTCCCGAAGGACT-CATGAGAGGCC (SEQ ID NO:54). The complementary oligonucleotides were annealed, producing NsiI and HindIII restriction sites (Promega Madison Wis.).

The fragments thus prepared were inserted into the pTR-UF21HP vector (provided by Dr. Christian Teschendorff, University of Florida), which had first been linearized with HindIII and SpeI restriction enzymes. Following insertion, the presence and correct orientation of the inserts was verified by DNA sequencing.

Figure 5:
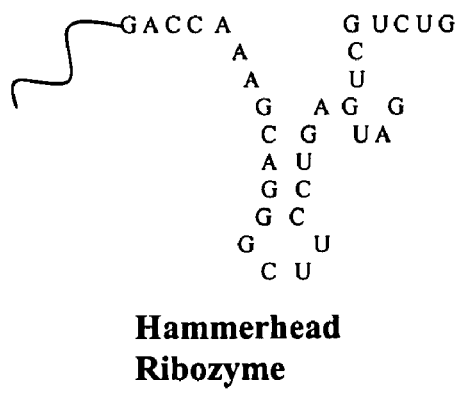
FIG. 5 is a schematic diagram of the structure of a self-cleaving hairpin ribozyme produced by the plasmid vector pTR-UF21, following insertion of a hammerhead ribozyme sequence into a cloning site in the vector, according to an embodiment of the invention. When transcribed, the self-cleaving hairpin ribozyme cleaves the sequence shown to the right of the hairpin cleavage site (arrow), with resultant production of the hammerhead ribozyme, shown on the left.
Figure 5:
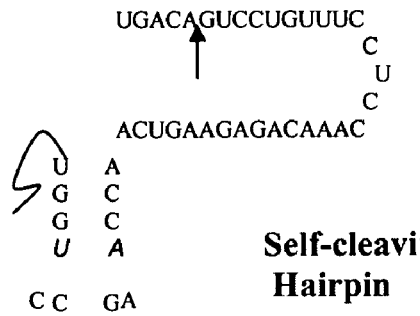
Figure 5:
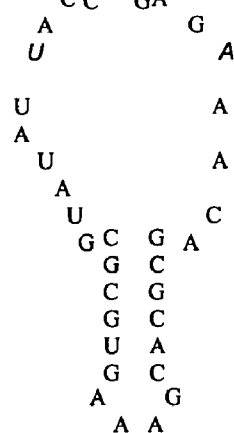

The pTR-UF21HP vector includes the chicken β-actin promoter and CMV enhancer to drive the synthesis of the ribozyme. The pTR-UF21 vector confers neomycin resistance. The pTR-UF21HP vector also contains a hairpin ribozyme following the hammerhead ribozyme insert site. Referring to FIG. 5, when transcribed in a cell, the mRNA product of this vector is a hairpin ribozyme connected to a hammerhead ribozyme encoded by the sequence inserted into the hammerhead cloning site. The hairpin ribozyme has the ability to self-cleave the mRNA, to yield the encoded hammerhead ribozyme with a relatively short 3' arm. This design has been found to improve cleavage efficiency.

Example 5

Cell Culture and Transfection with Ribozyme Plasmids

Cultures of human newborn foreskin fibroblasts (ATCC; Manassas, Va.) were cultured in equal parts Dulbecco's Modified Eagle Medium (DMEM), Medium 199 (Gibco BRL), Ham's F12 nutrient mixture (Gibco BRL) containing 1 mM NaHCO$_3$, and buffered with 25 mM HEPES at pH 7.4. The medium was supplemented with 10% heat-inactivated normal calf serum and 1×antibiotic-antimycotic (Gibco BRL).

Cell transfections were carried out using Lipofectamine reagent (Invitrogen Life Technologies; Carlsbad, Calif.). Exponentially growing cells were transfected with one of the following: vector alone (i.e., pTR-UF21), active CTGF ribozyme plasmid (i.e., pTR-UF21-CHR745), or inactive ribozyme plasmid (pTR-UF21-In). Cells that were stably transfected were selected on the basis of neomycin resistance using Geneticin (G418 Sulfate, Invitrogen Life Technologies Carlsbad, Calif.) Forty-eight hours after transfection, G418 was added to the culture medium at a concentration of 200 µg/ml. After 7 days, selected cells were transferred to 48-well plates.

Example 6

Detection of CTGF mRNA Transcripts by Quantitative Reverse-Transcription Polymerase Chain Reaction (Q-RT-PCR)

Cells in 48-well plates were held in serum-free medium for 48 hours. Then RNA was extracted using an RNeasy kit (Qiagen Valencia, Calif.). CTGF mRNA transcripts were detected using the TaqMan real-time quantitative RT-PCR procedure. A standard curve was generated using CTGF mRNA transcripts that were transcribed in vitro using T7 RNA polymerase from a plasmid containing a CTGF cDNA. CTGF transcript was precipitated with ethanol and dissolved in DEPC-treated water. Reactions were assembled in a 96-well optical reaction plate.

Each reaction contained 1×TaqMan One-step RT-PCR Master Mix, 900 nM forward primer (5'-AGCCGCCTCTG-CATGGT-3'; SEQ ID NO:55), 900 nM reverse primer (5'-CACTTCTTGCCCTTCTTAATGGTTCT-3'; SEQ ID NO:56), 2 µM fluorescent TaqMan probe, and RNA sample (CTGF mRNA standard, or 500 ng of sample RNA), to a final volume of 25 µL per reaction. The plate was analyzed on the ABI Prism 5700 Sequence Detection System (Applied Biosystem, Foster City, Calif.), which simultaneously performs the RT-PCR and detects fluorescence signal. A standard curve was generated using the transcribed CTGF mRNA samples ($2.3 \times 10^{-2}$ to $2.3 \times 10^{-6}$ pmol). The level of glyceraldehyde phosphate dehydrogenase (GAPDH) mRNA was also measured in each sample using the TaqMan GAPDH Control Kit (Applied Biosytems, Foster City Calif.), and the number of CTGF mRNA molecules in samples was expressed as pmol CTGF mRNA per pmol of GAPDH mRNA. Levels of mRNA were expressed as mean ± standard error of six replicate samples for each condition. NOVA and Tukey's HSD post-hoc tests were used to assess statistical significance between times and groups.

Example 7

CTGF Enzyme-linked Immunosorbent Assay (ELISA)

CTGF protein was measured in conditioned medium and in cytoplasmic extracts of serum-starved, cultured cells using a capture "sandwich" ELISA with biotinylated and non-biotinylated affinity purified goat polyclonal antibodies to human CTGF. Briefly, flat-bottom ELISA plates (Costar 96-well) were coated for 1 hour at 37° C. with 50 µL of goat anti-human CTGF antibody (provided by Dr. Gary Grotendorst), which predominately recognizes epitopes in the N-terminal half of the CTGF molecule. Concentration of antibody was 10 µ/mL in PBS/0.02% sodium azide. This antibody is appropriate for detection of rat CTGF because there is a 92% amino acid identity between the sequences of rat and human CTGF in the N-terminal half of the peptide (GenBank database). Wells were then washed four times and incubated with 300 µL of blocking buffer (PBS/0.02% sodium azide/1% bovine serum albumin) for 1 hour at room temperature.

The wells were subsequently washed four times, then 50 µL of sample or recombinant human CTGF protein (from 0.1 ng/ml to 100 ng/ml, provided by Dr. Gary Grotendorst) was added and incubated at room temperature for 1 hour. After washing, 50 µL of biotinylated goat anti-human CTGF (2 µg/mL) was added and incubated at room temperature in the dark for 1 hour, then washed, and 50 µL of alkaline phosphatase-conjugated streptavidin (1.5 µg/ml, Zymed, South San Francisco, Calif.) was added and incubated at room temperature for 1 hour. The wells were washed again and incubated with 100 µL of alkaline phosphatase substrate solution (1 mg/mL p-nitrophenyl phosphate, Sigma Chemicals, St. Louis, Mo.) in sodium carbonate/bicarbonate buffer/0.02% sodium azide, pH=9.6. Absorbance at 405 nm was measured using a microplate reader (Molecular Devices, Sunnyvale, Calif.).

CTGF levels were normalized for total protein content of samples using bicinchoninic acid (BCA) protein assay reagent (Pierce Chemical, Rockford, Ill.) and were expressed as ng/mg protein for six replicate samples for each condition. Sensitivity of the ELISA was 0.1 ng/ml with an intra-assay variability of 3%, which is similar to a previously published ELISA for CTGF (Tamatani T et al., *Biochem. Biophys. Res. Commun.* 251:745-752, 1998). Levels of protein were expressed as mean ± standard error of six replicate samples for each condition. Statistical significance between times and groups was assessed using ANOVA and Tukey's HSD post-hoc tests.

Example 8

Figure 6:
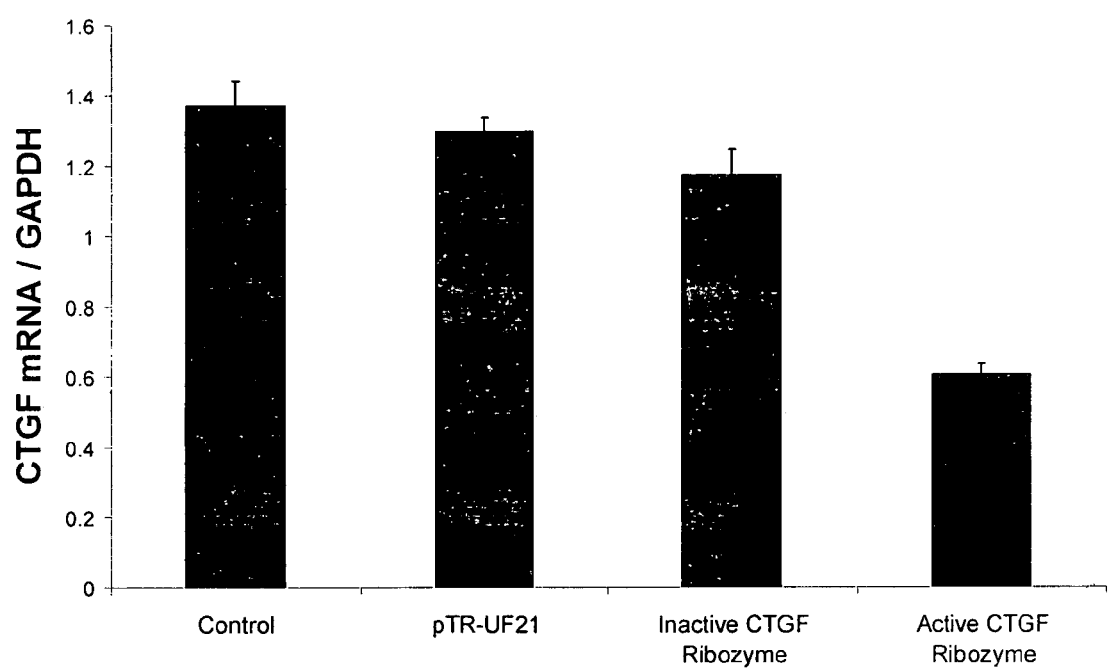
FIG. 6 is a graph showing the effect of a CTGF ribozyme on levels of CTGF mRNA expression in cultured human dermal fibroblasts, according to an embodiment of the invention. Cells were transfected with vector (i.e., pTR-UF21), inactive CTGF ribozyme plasmid, or active CTGF ribozyme plasmid. CTGF mRNA was measured using quantitative RT-PCR and results were normalized to GAPDH mRNA.

Effect of CTGF Ribozymes on CTGF mRNA Expression in Cultured Fibroblasts Transfected with CTGF Ribozymes Plasmids Cell cultures prepared and transfected as described above with plasmids expressing ribozyme CHR 859 or controls were examined for efficiency of cleavage of CTGF mRNA by the transfected cells. Expression of CTGF mRNA was measured by quantitative RT-PCR as described above. Referring to FIG. 6, the results showed that CTGF mRNA expression in CHR 859-transfected cells was decreased by 55% (p<0.01, n=6) compared with control groups. Thus the CTGF ribozyme was highly effective in reducing the level of CTFG mRNA expression in the cells.

Example 9

Figure 7:
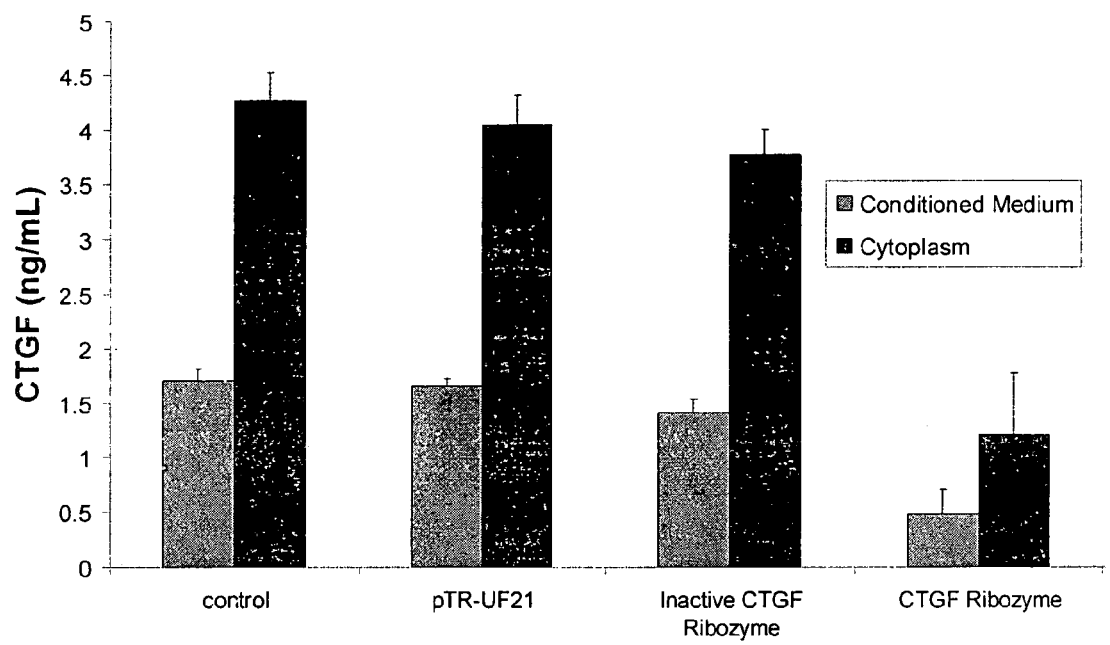
FIG. 7 is a graph showing the effect of CTGF ribozyme on levels of CTGF protein expression in cultured human dermal fibroblasts, according to an embodiment of the invention. Cells were transfected with vector (i.e., pTR-UF21), inactive CTGF ribozyme plasmid, or active CTGF ribozyme plasmid. CTGF protein was measured using a CTGF ELISA in cytoplasmic extracts and samples of conditioned medium.

Effect of CTGF Ribozymes on CTGF Protein Expression in Cultured Fibroblasts Transfected with CTGF Ribozyme Plasmids Human fibroblast cell cultures were transfected as described with plasmids expressing ribozyme CHR 859 or controls, and examined for production of CTGF protein. Expression of CTGF protein was measured by a "sandwich" ELISA, as described above, in conditioned medium from the cultures and in cytoplasmic extracts from the transfected cells. Referring to FIG. 7, in cells transfected with the active CTGF ribozyme, CTGF protein was significantly reduced, i.e., by 72% in conditioned medium and 71% in the cytoplasm, respectively, compared with control groups ($p<0.01$, $n=6$).

Example 10

TGF-$\beta$-Induced. Cell Proliferation Assay

TGF-$\beta$ is known to stimulate proliferation of fibroblasts in culture (Gabrielson EW et al., FASEB J 2: 2717-2721, 1988). CTGF is a putative mediator of TGF-$\beta$-induced proliferation by cells in culture.(Grotendorst GR, Cytokine Growth Factor Rev 8: 171-179, 1997). To determine effects of CTGF mRNA-targeting ribozymes on TGF-$\beta$-induced cellular proliferation, transfection experiments followed by proliferation assays were performed using human fibroblast cultures as follows. Experiments utilized four groups of cells: 1) non-transfected control cells, and three types of transfected cells, i.e., cells transfected with 2) plasmid vector alone (pTR-UF21); 3) active CTGF ribozyme plasmid; or 4) inactive CTGF ribozyme plasmid. All cells were seeded in 48-well tissue culture plates (seeding density, 5000 cells per well) and cultured for 48 hours in serum-supplemented medium.

Cells were then subjected to a 48 hour period of serum starvation. The cultures were subsequently stimulated to proliferate by the addition of 5 ng/mL recombinant human TGF-$\beta$1 (R&D Systems; Minneapolis, Minn.). Cell proliferation in the cultures was measured 24 hr later using a non-radioactive MTS cell proliferation assay (Promega; Madison, Wis.). Absorbance readings corresponding to cell proliferation were expressed as mean ± standard error of six replicate samples for each condition. ANOVA and Tukey's HSD post-hoc tests were used to assess statistical significance.

Example 11

Effect of CTGF Ribozymes on TGF-$\beta$-Induced Cell Proliferation

Figure 8:
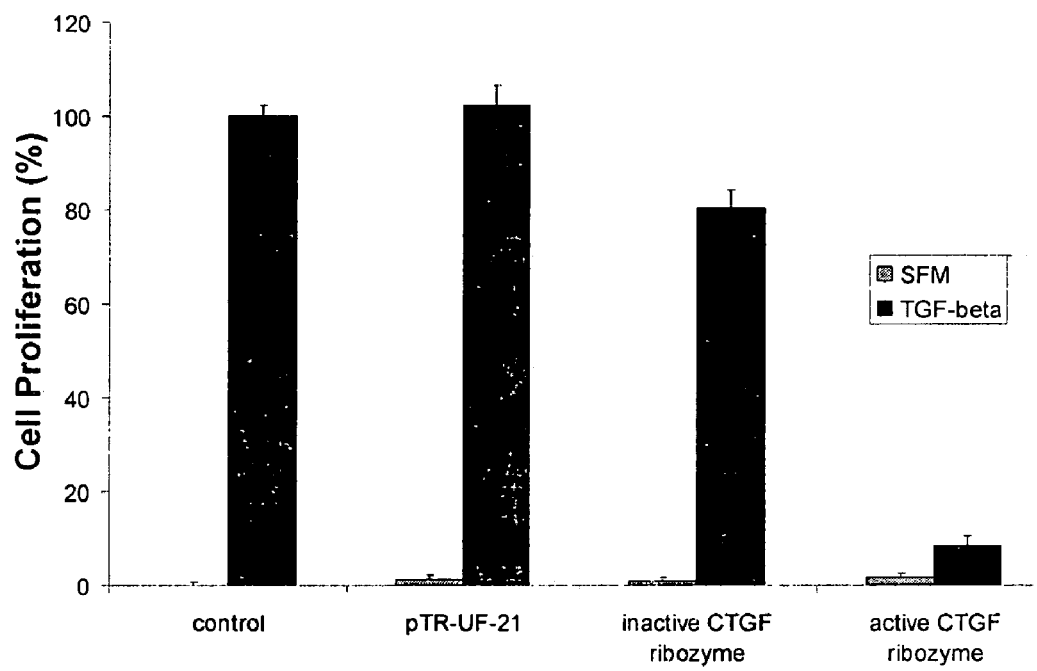
FIG. 8 is a graph showing the effect of CTGF ribozyme on TGF-β-induced cell proliferation in cultured human fibroblasts, according to an embodiment of the invention. Cells were transfected with vector, inactive ribozyme plasmid, or active ribozyme plasmid and maintained in either serum-free medium (SFM) or medium containing 10 ng/mL TGF-β1 24 hours before assaying. Data are normalized based on control cells in SFM (0% proliferation) and control cells treated with TGF-β(100% proliferation).

Cultured human fibroblasts, either untransfected or transfected with pTR-UF21 vector, inactive CTGF ribozyme or active CTGF ribozyme were assayed for TGF-$\beta$-induced cell proliferation as described above. Referring to FIG. 8, no proliferation was observed in cells maintained in serum-free medium. In response to addition of TGF-$\beta$, maximal proliferation was observed in untransfected control cells and cells transfected vector alone. By contrast, cells transfected with the vector expressing active ribozyme targeting CTGF mRNA showed a marked decrease (90%, $p<0.01$, $n=6$) in cell proliferation when compared to control cell groups. Cells transfected with inactive ribozyme expressing vector did not show this inhibitory effect, proliferating at about 80% of contol rates. Combined results of these experiments implied that the active CTGF ribozymes not only acted to decrease CTGF mRNA and protein expression and secretion, but further produced a separate physiological effect, i.e., that of interfering with the TGF-$\beta$-mediated proliferative response.

Example 12

Ribozyme-Mediated Reduction of CTGF mRNA and Protein Expression in Transfected Human Corneal Fibroblasts Human corneal fibroblasts were cultured essentially as described above. Plasmid DNAs containing 1) vector alone, 2) CTGF ribozyme 859, or 3) inactive ribozyme control targeting the same CTGF sequence, were used to transfect the corneal fibroblasts using the calcium phosphate co-precipitation method. After two days, cells were harvested and total RNA was extracted. The level of CTGF mRNA was measured using quantitative RT-PCR essentially as described above, and compared to the level of $\beta$-actin mRNA in the same cells.

Figure 9:
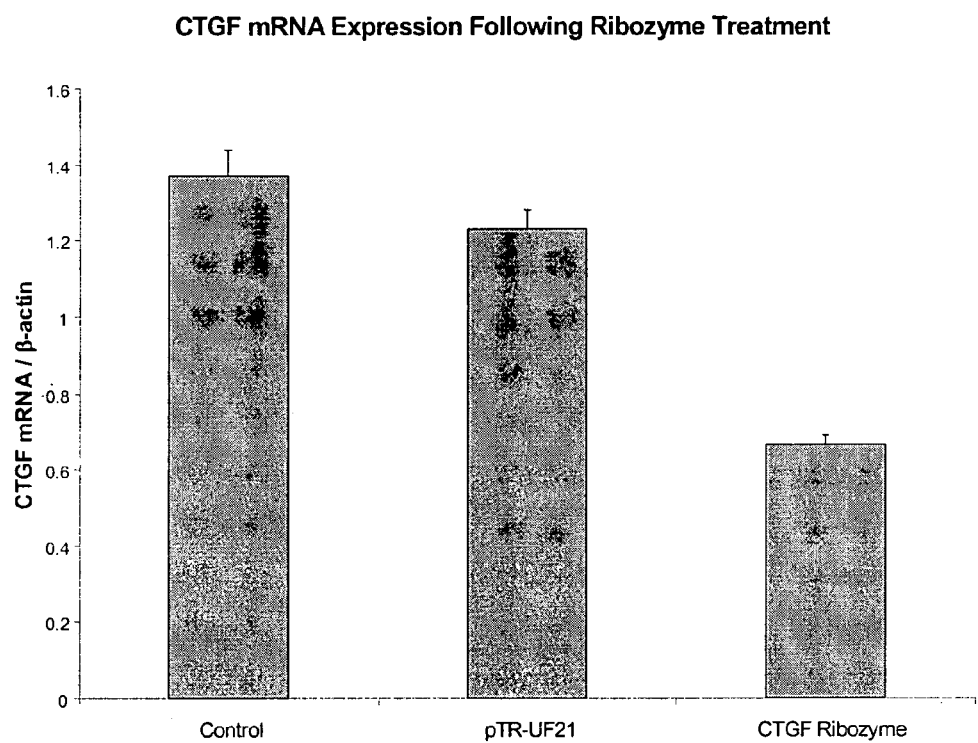
FIG. 9 is a graph showing reduction of CTGF mRNA expression in human corneal fibroblasts following transfection with active CTGF ribozyme, but not control vector devoid of ribozyme, according to an embodiment of the invention.

Referring to FIG. 9, results showed that relative to untransfected cells, cells transfected with the CTGF ribozyme demonstrated a 45% reduction in CTGF mRNA. By contrast, transfection with the pTR-UF21 vector devoid of ribozyme had no significant effect on CTGF expression by the cells (FIG. 9).

Figure 10:
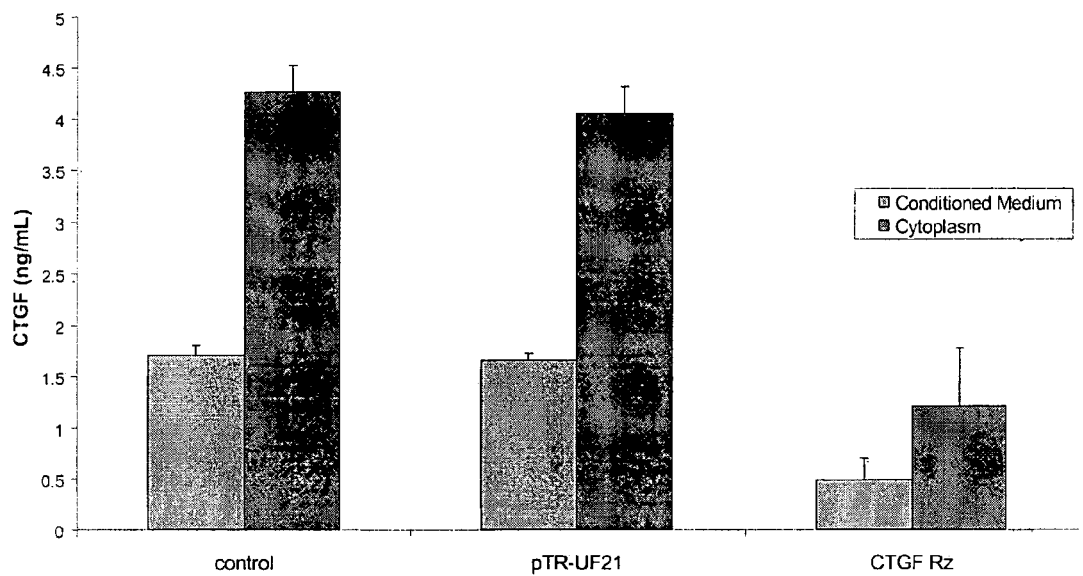
FIG. 10 is a graph showing reduction of CTGF protein expression in conditioned medium and cell lysates of human corneal fibroblasts following transfection with active CTGF ribozyme, but not control vector, according to an embodiment of the invention.

Levels of CTGF protein expression were also analyzed in the human corneal fibroblasts. As seen in FIG. 10, this ribozyme also resulted in a reduction (>60%) in both the secreted and the intracellular forms of CTGF protein, based on ELISA of the conditioned culture medium and of the cytosolic fraction. Again, vector alone has no such effect. Similarly, an inactive ribozyme that recognizes the same sequence had no impact on CTGF protein levels. These results demonstrate that plasmid-delivered ribozymes can exert a significant inhibitory effect on CTGF synthesis in an ocular cell type (i.e., corneal fibroblasts) that is the site of several scarring conditions of the eye.

Example 13

In Vivo Testing of CTGF Ribozymes in Animal Models of Corneal Scarring

Bilateral PRK ablation is performed on adult Sprague Dawley male rats (220-250 grams) free of disease as described (Chen C et al., *Invest. Ophthaloml. Vis. Sci*. 2000; 41:4108-4116.) One eye of each rat is treated with 50 µl of vehicle (for example, PBS) containing 100 µg of the test composition, such as 1) plasmid expressing a ribozyme or 2) plasmid expressing a corresponding inactive ribozyme. The other eye is treated with 50 µl of vehicle alone. At selected intervals, for example, 7, 14, and 21 days after PRK ablation and treatment, the rats are anesthetized and the corneas are evaluated by slit lamp biomicroscopy for the level of corneal haze. Corneas are graded using a scale from 0 to 4 (0=clear cornea; 1=trace of haze; 2=slight haze, iris detail visible; 3=moderate haze, iris detail not visible; 4=severe haze, pupil only visible). Scores are compared for statistical differences, for example using Wilcoxson's non-parametric paired ranking test. Typically, 10 rats are evaluated for each test composition.

At the end of the evaluation period, the corneas are excised and bissected. Half of the tissue is processed for histological evaluation as described below, and the other half is analyzed biochemically for CTGF mRNA and protein expression as previously described.

For histological evaluation, corneas are fixed briefly in 4% paraformaldehyde and frozen or paraffin sections are prepared. Sections are stained with standard hemotoxylin and eosin stain, and van Giesson stain or Mason's trichrome for detection of new collagens. Sections are also immunostained with antibodies that specifically bind to collagen types I, III, and IV (antibodies from Santa Cruz Biotechnology), and to γ-smooth muscle actin (antibodies from Chemicon).

Example 14

Involvement of CTGF in Subepithelial Fibrosis (SF)

This example provides evidence of involvement of CTGF in subepithelial fibrosis (SF) observed in bullous keratopathy. Accordingly, this disease may be a candidate for therapeutic intervention using a ribozyme of the invention.

SF is known to occur in various corneal diseases. Accumulation of fibrotic substances and extracellular matrix components are prominent in the disease, although the underlying pathophysiology is presently unknown. To investigate the role of CTGF in SF of bullous keratopathy, sections from twenty surgical specimens of corneal buttons received after corneal transplantation were prepared and subjected to immunohistochemical staining with specific antibodies against human CTGF, followed by analysis by light microscopy.

Results from the tissue analysis revealed patchy accumulation of specific staining for CTGF in the subepithelial regions of the corneas. No specific staining was observed in the deeper parts of the corneal stroma. Control sections were negative. These results indicate that a contribution of CTGF in the process of subepithelial fibrosis is very likely in cases of bullous keratopathy.

Example 15

Involvement of CTGF in Fibrous Dysplasia

This example describes an analysis of CTGF involvement in orbito-facial pathology.

Fibrous dysplasia (FD) is a slowly progressive relatively rare fibrotic bone disease that may be either monostotic or polyostotic. When present in a cranio-maxillo-facial location, opthalmological sequelae can result due to the proximity of the orbit and the optic canal. To determine the role of CTGF in FD, immunohistochemical staining with specific antibodies against CTGF was performed as described above on surgical specimens obtained from four FD patients One out of the four cases examined demonstrated specific staining for CTGF. The staining appeared mainly in close proximity to fibroblasts, selectively in areas with considerable accumulation of fibrosis. In this case, the fibrous dysplasia was still active. In all sections of the other three samples, no specific staining was detectable. These results demonstrate that CTGF may be expressed in pathologically active fibrous dysplasia. Hence this factor may be involved in the pathophysiology of this condition, adding to the list of conditions that may benefited by treatment with the ribozymes of the invention.

Example 16

Polyzymes Based on CTGF

This example describes an embodiment of the invention in which multiple ribozymes are linked in tandem to form a "polyzyme."

Reducing levels of CTGF mRNAs by targeting multiple sites within the CTGF mRNA may reduce CTGF levels even more effectively than targeting individual sites within the mRNA molecule, as demonstrated in the examples above. To construct a polyzyme, individual ribozymes that cut at distinct sites in the CTGF mRNA and that preferably are separately effective in reducing CTGF expression are linked in tandem to construct a poly-ribozyme ("polyzyme"). Coding sequences for polyzymes are cloned into vectors containing for example the promoter of T7 RNA polymerase, and tested against individual targets in vitro to verify that the multimeric ribozymes retain their activity. Active polyzymes are then cloned into eukaryotic expression vectors for use in cells and in animals.

Figure 11:
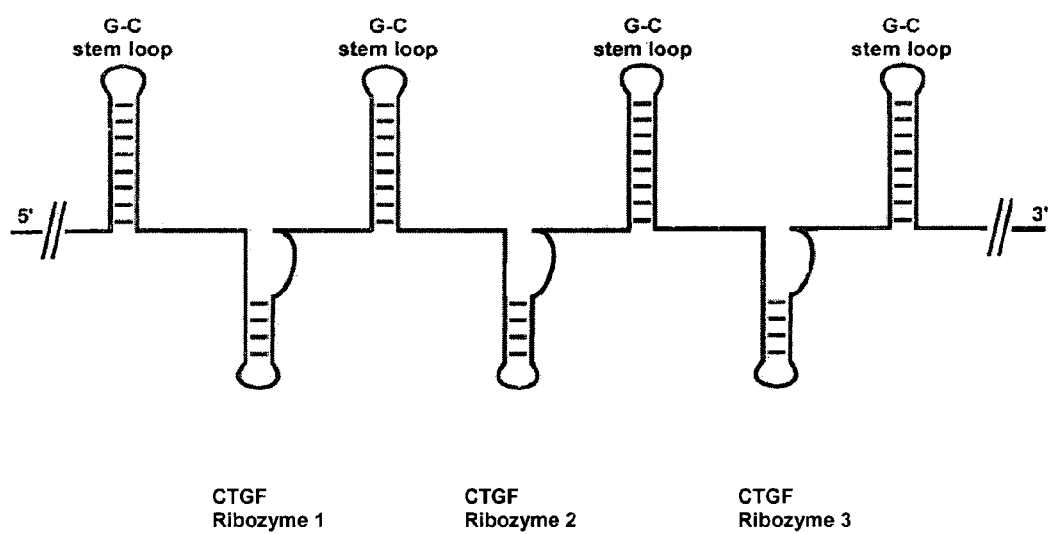
FIG. 11 is a schematic diagram illustrating the structure of a CTGF polyzyme, according to an embodiment of the invention.

Methods of making multimeric ribozymes of up to nine individual hammerhead ribozymes that can effectively inhibit expression of viral and nuclear genes have been described (Ramezani, A. et al., 1997, *Gene Therapy* 4: 861-867, 1997; Shen, T. J. et al., 1999, *Blood Cells Mol. Dis.* 25:361-373; O'Neill, B. et al., 2000, *Invest. Ophthalmol. Vis. Sci.* 41: 2863-2869; Bai, J. et al. 2001, *AIDS Res. Hum. Retroviruses* 17: 385-399). It has been demonstrated that ribozyme sequences can be simply strung together, separated by restriction sites, without substantially reducing the cleavage efficiency of each unit. Alternatively, to ensure independent folding of ribozyme monomers, the ribozymes can be separated using a G-C rich stem-loop structure, for example as described (Seyhan, A. A. et al., 2002, *J. Biol. Chem.* 277: 25957-25962). Stems of 8 base pairs are capped by RNA tetraloops, for example having the sequence UUCG (SEQ ID NO:57) to nucleate first-order folding of the stem-loop. Such stems serve to both isolate ribozymes into folding units and to protect them from exonucleolytic degradation. Predicted folding of the polyzymes is checked using an algorithm such as Mfold, to minimize the likelihood of creating an inactive ribozyme having an inappropriate secondary structure. A diagram showing a design for a CTGF polyzyme according to one embodiment of the invention is shown in FIG. 11.

Polyzymes and punctuating stem-loops are cloned by annealing and extension of overlapping oligonucleotides. Terminal oligonucleotides are added, for example, at a concentration of 10 pmol and internal oligos are added, for example at 1 pmol. The extension reaction can utilize thermostable Pfu polymerase, which has proofreading capacity, and the number of annealing and extension cycles is determined experimentally. Typically, 60-80 nucleotide segments overlapping by 20 base pairs are designed so that the annealing temperature for all overlaps is the same. This approach has been used to construct genes up to 1.3 kb (Guy, J. et al., 2002, Ann.Neurol. 52:534-542). As an example, four ribozymes (for example of 33 nt in length) and five flanking stem-loops (for example, of 20 nt in length) can be constructed with only four oligonucleotides. Full length extension products are cloned into a vector containing the promoter for T7 RNA polymerase (such as pT7/T13-18) and their integrity is confirmed by DNA sequence analysis.

For testing the efficacy of polyzymes, polymeric ribozymes are first transcribed in vitro using T7 RNA polymerase. The polyzymes are tested on each separate target by time course analysis of cleavage as described above. If an individual ribozyme performs poorly in the context of the polyzyme (i.e., if its observed rate of cleavage is diminished relative to its activity as a monomer), it is either replaced with an alternative ribozyme targeting another site, or its sequence context is modified, for example by changing or eliminating the flanking stem-loop.

Ribozyme combinations that perform well in the test tube are tested in cell lines as follows. Polyzymes are cloned in a vector such as the pTRUF21 vector using PCR, to amplify the polyzyme and to add appropriate flanking restriction sites (for example, HindIII and SpeI). The vectors are used to generate stable polyzyme-expressing cell lines in an appropriate cell line, such as Vero cells, using antibiotic (for example, G418) selection. The cells lines are used to test the efficacy of the polyzymes at cleaving CTGF.

Other Embodiments

While the above specification contains many specifics, these should not be construed as limitations on the scope of the invention, but rather as examples of preferred embodiments thereof. Many other variations are possible. Accordingly, the scope of the invention should be determined not by the embodiments illustrated, but by the appended claims and their legal equivalents.

What is claimed is:

1. A ribozyme that specifically cleaves a target RNA sequence encoded by a CTGF gene, said ribozyme encoded by a nucleic acid comprising a sequence of SEQ ID NO:48.

2. The ribozyme of claim 1, wherein the ribozyme is present in a hammerhead configuration.

3. The ribozyme of claim 2, wherein the ribozyme specifically cleaves target RNA sequences encoded by CTGF nucleotide sequence SEQ ID NO:50.

4. An expression vector comprising an isolated nucleic acid encoding a CTGF ribozyme of SEQ ID NO:48.

5. The expression vector of claim 4, wherein said vector is a plasmid.

6. The expression vector of claim 5, wherein the plasmid directs synthesis of a self-cleaving hairpin ribozyme attached to a CTGF ribozyme in a hammerhead configuration.

7. The expression vector of claim 6, wherein the plasmid is pTRUF21.

8. A method for reducing CTGF mRNA or protein in a cell, the method comprising the steps of: (a) group providing a tissue comprising a cell expressing a target RNA sequence encoded by a CTGF gene;and (b) contacting said tissue with a vector comprising a nucleic acid that encodes at least one ribozyme that specifically cleaves a target RNA sequence encoded by a CTGF gene, in an amount effective to reduce said CTGF MRNA or protein expression in said cell, wherein said at least one ribozyme is encoded by a nucleic acid comprising a sequence of SEQ ID NO:48 or a complement of SEQ ID NO:48.

9. The method of claim 8, wherein said cell is a fibroblast.

10. The method of claim 8, further comprising contacting said tissue with said vector in a subject having or at risk for developing a condition causing a scar in said tissue.

11. The method of claim 10, wherein said condition is a fibrotic disorder.

12. The method of claim 11, wherein said fibrotic disorder is selected from the group consisting of scleroderma, keloids, liver cirrhosis, kidney fibrosis, peritoneal adhesions, tendon adhesions, breast implant capsule adhesions, burn scars spinal cord injuries, bile duct atresia, subepithelial fibrosis, fibrous dysplasia, and tympanic membrane fibrosis.

13. The method of claim 11, wherein said condition is wound healing following surgery.

14. The method of claim 13, wherein said surgery is corneal surgery.

15. The method of claim 13, wherein said surgery is glaucoma filtering surgery.

16. The method of claim 8, wherein said tissue is an ocular tissue selected from the group consisting of cornea, conjunctiva, sciera and trabecular meshwork.

* * * * *

UNITED STATES PATENT AND TRADEMARK OFFICE
CERTIFICATE OF CORRECTION

PATENT NO. : 7,462,602 B2  Page 1 of 1
APPLICATION NO. : 10/836670
DATED : December 9, 2008
INVENTOR(S) : Gregory S. Schultz et al.

It is certified that error appears in the above-identified patent and that said Letters Patent is hereby corrected as shown below:

Column 1, line 18, delete "the U. S. government may have certain rights" and insert therefor --the U. S. government has certain rights--

Signed and Sealed this

Eleventh Day of August, 2009

David J. Kappos
*Director of the United States Patent and Trademark Office*